(12) United States Patent
Frances et al.

(10) Patent No.: US 8,916,624 B2
(45) Date of Patent: Dec. 23, 2014

(54) DENTAL COMPOSITIONS CROSSLINKABLE/POLYMERIZABLE BY CATIONIC PROCESS

(75) Inventors: Jean-Marc Frances, Meyzieu (FR); Sophie Schneider, Ternay (FR)

(73) Assignee: Bluestar Silicones France SAS, Lyons (FR)

( * ) Notice: Subject to any disclaimer, the term of this patent is extended or adjusted under 35 U.S.C. 154(b) by 17 days.

(21) Appl. No.: 12/765,236

(22) Filed: Apr. 22, 2010

(65) Prior Publication Data

US 2011/0189632 A1  Aug. 4, 2011

Related U.S. Application Data

(63) Continuation of application No. 12/374,612, filed as application No. PCT/EP2007/057466 on Jul. 19, 2007, now abandoned.

(30) Foreign Application Priority Data

Jul. 21, 2006  (FR) ..................................... 06 06644

(51) Int. Cl.
*A61K 6/08* (2006.01)
*A61K 6/087* (2006.01)
*A61K 6/00* (2006.01)
*A61K 6/093* (2006.01)

(52) U.S. Cl.
CPC ................ *A61K 6/093* (2013.01); *A61K 6/0088* (2013.01); *A61K 6/0052* (2013.01)
USPC ........ 523/116; 523/113; 523/115; 433/228.1; 106/35; 522/148; 522/168; 522/170

(58) Field of Classification Search
CPC ....... A61K 6/08; A61K 6/087; A61K 6/0088; A61K 6/005; A61K 6/0002
USPC .......... 523/116, 113, 115; 433/228.1; 106/35; 522/148, 168, 170
See application file for complete search history.

(56) References Cited

U.S. PATENT DOCUMENTS

| 7,247,660 | B2 | 7/2007 | Frances | |
|---|---|---|---|---|
| 7,740,482 | B2 * | 6/2010 | Frances et al. | 433/215 |
| 2004/0186202 | A1 | 9/2004 | Klettke et al. | |
| 2005/0261390 | A1 * | 11/2005 | Frances et al. | 522/172 |
| 2005/0277705 | A1 * | 12/2005 | Frances | 523/115 |

(Continued)

FOREIGN PATENT DOCUMENTS

| WO | WO 00/19966 A1 | 4/2000 |
|---|---|---|
| WO | WO 00/19967 A1 | 4/2000 |

(Continued)

OTHER PUBLICATIONS

International Search Report issued on Oct. 20, 2008 in International Patent Application No. PCT/EP2007/057466 and an English language translation thereof.

(Continued)

*Primary Examiner* — Michael Pepitone
(74) *Attorney, Agent, or Firm* — Dentons US LLP

(57) ABSTRACT

Improvedly storage stable dental compositions useful for the preparation of dental prostheses and for dental restoration containing a uniquely pretreated dental filler material.

26 Claims, No Drawings

(56) References Cited

U.S. PATENT DOCUMENTS

2006/0178444 A1     8/2006   Frances
2008/0287562 A1*   11/2008   Frances et al. .................... 522/7
2009/0258961 A1    10/2009   Frances

FOREIGN PATENT DOCUMENTS

WO     WO 2005/027857 A1    3/2005
WO     WO 2005/120439 A1   12/2005
WO     WO 2005/121200 A1   12/2005

OTHER PUBLICATIONS

English language translation of the Written Opinion of the International Searching Authority issued on Feb. 17, 2009 in International Patent Application No. PCT/EP2007/057466.

\* cited by examiner

DENTAL COMPOSITIONS CROSSLINKABLE/POLYMERIZABLE BY CATIONIC PROCESS

CROSS-REFERENCE TO RELATED APPLICATIONS

This application is a continuation of U.S. application Ser. No. 12/374,612, filed on Jan. 21, 2009, now abandoned, which is a national phase of International Application PCT/EP07/57466, filed on Jul. 19, 2007, which claims the benefit of priority of FR 0606644, filed Jul. 21, 2006, each hereby expressly incorporated by reference in its entirety.

The field of the invention is that of dental compositions. More precisely the dental compositions developed in the context of the present invention can be used for producing dental prostheses and for dental restoration.

These dental compositions are conventionally epoxy resins or photopolymerizable silicones or free-radically polymerizable acrylate resins. These compositions further include particulate reinforcing fillers (e.g. of hydrophobicized silica), photo-initiators and, optionally, photosensitizers and even other functional additives such as pigments or stabilizers.

When they have been mixed, these compositions are shaped and then photocrosslinked to a mass whose structure is similar to that of the teeth.

The fact that the filler is composed of very fine particles (≈0.01 to 5 μm) with a high specific surface area is a factor which limits its degree of incorporation into the resin. This is because the absorption capacity of the resin is limited. As a result of this, the filler levels of such compositions rarely attain more than 45% by volume. This is therefore to the detriment of the mechanical reinforcement function assigned to the particulate filler.

Moreover, dental compositions are formulated with reinforcing fillers such as inorganic glasses or fumed silicas with a very low particle size, in which the surface silanols and/or the residual water react with the cationic functions, which does not allow the compositions to be stored. The same is true when these glasses or these fumed silicas are pretreated with silanes such as glycidyloxypropyltrimethoxysilane or glycidyloxypropyltriethyoxysilane or even methacryloyl-oxypropyltrimethoxysilane. The reinforcing fillers interact with the reactive functions of the (photo)polymerizable/crosslinkable species and are therefore a cause of problems of instability of the dental composition in the course of its storage, which may reach durations of several months. This phenomenon of instability on storage is accentuated for highly filled compositions (e.g. overall filler level≥50%).

U.S. Pat. No. 6,306,926 relates to dental compositions based on epoxy resins (e.g. UVR® 6105, EPON® 828, GY281®), oxetane resins or vinyl ether resins, among others, which are polymerizable/crosslinkable, cationically and under irradiation, and optionally (meth)acrylate resins which are polymerizable free-radically. In addition to the polymerization initiators, as represented by the cationic photo-initiators and optionally the free-radical initiators, as appropriate, these compositions include a microparticulate mineral filler which is radioopaque and is selected from the following metal compounds: oxides, halides, borates, phosphates, silicates, carbonates, germanates, tetrafluoroborates, and hexafluorophosphates, having an isoelectric point of less than 7. This composition is such that its Barcol hardness is at least 10 after 30 minutes of cationic polymerization at 25° C.

A drawback of these resins is that they are not perfectly transparent to the actinic activating radiation of the polymerization by UV-visible radiation, and this is detrimental to the reaction kinetics and therefore limits the possibilities of obtaining very thick photocrosslinked materials.

Patent application FR-A-2 784 025 is aimed at remedying this problem by proposing dental compositions based on silicone resins which are polymerizable/crosslinkable, cationically and under irradiation, with or without subsequent thermal post-crosslinking. These silicone resins contain oxirane (epoxide, oxetane, etc.) or vinyl ether functionalities. Such compositions comprise:
  one or more polydimethylsiloxanes which are crosslinkable and/or polymerizable cationically and which carry, on at least one of their ends, reactive functions of formula:

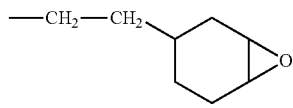

an effective amount of at least one ionium borate initiator:

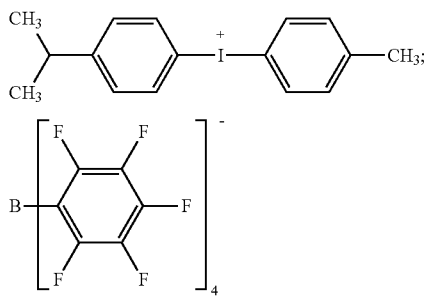

at least one photosensitizer, and
at least one inert, reinforcing or dental filler which is based on dental glasses or on polymethyl methacrylate or on optionally hexamethyldisilazane- or polydimethylsiloxane-treated fumed silica with a specific surface area of 200 m²/g.

These dental compositions are intended for the manufacture of prostheses or dental devices and for dental restoration.

These silicones have the advantage over organic resins which crosslink cationically of being highly transparent to UV-visible light and hence of allowing very thick materials (several millimeters thick) to be obtained which are photocrosslinked within a very short time (less than one minute) with a UV lamp which emits in the visible field>400 nm.

These silicones, however, are formulated with reinforcing fillers that have Lewis or Brønstedt acid character, such as ground glasses or fumed silicas of very low particle size, in which the surface silanols and/or the residual water react with the cationic functions. Silicone formulations of this kind are therefore unstable on storage. Moreover, when the silicones are formulated with thioxanthone photo-sensitizers, a high level of color variation is observed when they are exposed for photocrosslinking. This is manifested in a pinky coloring of the end product (after exposure) which is esthetically undesirable.

Also known, through patent application EP-A-1 050 291, are highly charged dental compositions which are presented as being endowed with good mechanical properties and contain from 10% to 70% by volume of filler (e.g. fumed silica) with a particle size (Φm) of between 0.05 and 0.5 μm (less than 50% by volume of particles with a diameter Φ>0.50 μm), a free-radically photopolymerizable acrylic monomer and a phosphoric ester dispersant of formula:

$$R-[-CO-(CH_2)_5-O-]_n-PO_3H_2.$$

However, the problems of stability on storage of the dental compositions are not dealt with in that reference.

Finally, international application WO-A-2005121200 describes highly charged cationic dental compositions comprising: at least one cationically reactive compound (A); at least one dental filler (B); optionally at least one dispersant (C), comprising at least one organic polymer or copolymer; at least one cationic photoinitiator; and optionally at least one photosensitizer (E), said composition being characterized in that at least one dental filler (B) is treated: with at least one organosilicon coupling agent (F) and with at least one compound (G), said organo-silicon coupling agent (F) comprising at least one reactive function (frA) which is directly bonded to a silicon atom which forms, after activation, a chemical bond with the dental filler, and at least one reactive function (frB) which is not directly bonded to a silicon atom which forms, after activation, a chemical bond with a reactive function (frC) of the compound (G).

Although these compositions constitute an improvement in relation to the prior art, it is nevertheless desirable to improve these compositions in terms of storage stability.

It is therefore apparent that the prior art provides no satisfactory solution to the problem of storage stability of dental compositions based on units which are cationically UV-polymerizable (oxiranes, for example).

One of the key objectives of the present invention is therefore to remedy this situation by providing new dental compositions which are based on units which are cationically UV-polymerizable (oxiranes, for example) which do not have the drawbacks of the prior art from the standpoint of storage stability.

Another key objective of the present invention is to provide new cationic dental compositions, which are polymerizable and/or crosslinkable in an oral environment, which not only are stable on storage and highly filled (e.g. ≥50%) but which also have the advantage of being highly transparent to UV-visible light and hence of allowing very thick materials (several millimeters thick) to be obtained which are photo-crosslinked within a very short time (less than one minute) with a UV lamp which emits in the visible field>400 nm.

Another key objective of the present invention is to provide new cationic dental compositions which are polymerizable and/or crosslinkable in the oral environment, and which are stable, highly charged (e.g. ≥50%), easy to prepare, and economical.

Another key objective of the present invention is to provide a new process for treating a dental reinforcing filler in such a way that it is able to meet the constraints set out above when it is used in particular as a reinforcing filler in a dental composition.

These objectives, among others, are achieved by the present invention, which first provides a dental composition comprising:
(1) at least one cationically reactive compound (A);
(2) at least one dental filler (B);
(3) optionally at least one dental filler (B');
(4) optionally at least one dispersant (C), comprising at least one organic polymer or copolymer;
(5) at least one cationic photoinitiator (D); and
(6) optionally at least one photosensitizer (E), said composition being characterized in that the dental filler (B) is pretreated in a solvent medium by contacting it with the following ingredients (a), (b), and (c):

(a) at least one compound (G) which is:
  an organic monomer, oligomer or polymer, or
  an organosiloxane monomer, oligomer or polymer, said compound (G) comprising at least one reactive oxirane, oxetane, alkenyl ether and/or carbonate function (frC),
(b) at least one organosilicon coupling agent (F) comprising at least one reactive function (frA) bonded directly to a silicon atom capable of reacting with the dental filler (B), and at least one reactive function (frB) not directly bonded to a silicon atom capable of reacting with a reactive function (frC) of the compound (G), and
(c) at least one dispersant (H) which maintains the dental filler (B) in a nonagglomerated form during and/or after the treatment in a solvent medium.

It is to the inventors' merit to have shown, surprisingly and unexpectedly, that when a dental filler is pretreated in a solvent medium with specific chemical species according to the invention, the presence of a dispersant prevents the formation of agglomerate and enhances the storage stability of the dental compositions formulated with this type of filler. This stability is manifested in a useful life of several months or years.

This technical solution is of all the more interest for being economically viable and simple to implement.

In one preferred embodiment, the dispersant (H) is an organic polymer or copolymer or a carboxylic acid monodiester.

In a second preferred embodiment, the dispersant (H) is selected from the group consisting of:
  acrylic polymers optionally in the form of a salt with an alkylammonium, polyesters, polyethers, polyurethanes, modified polyurethanes, and polyacrylate polyols,
  copolymers thereof,
  carboxylic acid monodiesters,
  polyurethane/acrylate copolymers, optionally in the form of a salt with an alkylammonium, and
  mixtures thereof.

Useful examples of dispersant (H) are as follows: polyurethane/acrylate copolymers, optionally in the form of a salt with an alkylammonium, acrylic copolymers, optionally in the form of a salt with an alkylammonium, carboxylic acid monodiesters, polyesters, polyethers, polyurethanes, modified polyurethanes, polyacrylate polyols, copolymers thereof or mixtures thereof. The dispersants sold under the brand name Disperbyk® (from Byk) or Solsperse® (from Avecia) are particularly suitable for the invention. Included in particular and by way of example are the following commercial products: Disperbyk® 164, Disperbyk® 161, Disperbyk® 166, Disperbyk® 2070, Disperbyk® 9075, Disperbyk® 9076.

Further dispersants include those cited in the following patents:
U.S. Pat. No. 5,882,393 which describes dispersants based on polyurethanes/imidazole acrylates or epoxides;
U.S. Pat. No. 5,425,900 which describes dispersants based on polyurethanes;
U.S. Pat. No. 4,795,796 which describes dispersants based on polyurethanes/polyoxyalkylene glycol monoalkyl ethers;
patent application WO-A-99/56864 which describes dispersants based on polyurethanes/poly(oxyalkylene-carbonyl)s: derivatives of ε-caprolactone and of δ-valerolactone; and
patent EP-B-0 403 197 which describes grafted polyacrylate polyol dispersants comprising a random polyurethane/polyvinyl/polyacrylate copolymer and a polyoxyalkylene polyether.

In another preferred embodiment:
- the reactive function (frA) bonded directly to a silicon atom of the organisilicon coupling agent (F) is an alkoxy, enoxy or hydroxyl function;
- the reactive function (frB) not bonded directly to a silicon atom of the organosilicon coupling agent (F) is an oxirane, oxetane, hydroxyl, acid, carboxylic acid anhydride or diol function; and
- the reactive function (frC) of the compound (G) is an oxirane, oxetane, alkenyl ether or carbonate function.

According to one preferred version of the invention, the dental composition of the invention comprises at least one dental filler (B) treated by a process (I) comprising the following steps:

a) in a solvent medium the dental filler (B) and at least one organosilicon coupling agent (F) as defined above are mixed,
b) the solvent is removed by filtration to give an intermediate dental filler (B-1),
c) the intermediate dental filler (B-1) undergoes a heat treatment to terminate the coupling reaction between the intermediate dental filler (B-1) and the coupling agent (F) and so to obtain an intermediate dental filler (B-2),
d) the intermediate dental filler (B-2) is then mixed in a solvent medium with at least one compound (G) as defined above and in the presence of at least one dispersant (H) as defined above,
e) the solvent is removed by filtration to give an intermediate dental filler (B-3), and
f) the intermediate dental filler (B-3) undergoes a heat treatment to terminate the reaction between the intermediate dental filler (B-3) and the compound (G) and so to obtain a treated dental filler (B).

According to another preferred version of the invention, the dental composition of the invention comprises at least one dental filler (B) treated by a process (II) comprising the following steps:

a) in a solvent medium the dental filler (B) and at least one organosilicon coupling agent (F) as defined above are mixed,
b) the solvent is removed by filtration to give an intermediate dental filler (B-1),
c) the intermediate dental filler (B-1) undergoes a heat treatment to terminate the coupling reaction between the intermediate dental filler (B-1) and the coupling agent (F) and so to obtain an intermediate dental filler (B-2),
d) the intermediate dental filler (B-2) is then mixed in a solvent medium with at least one compound (G) as defined above,
e) the solvent is removed by filtration to give an intermediate dental filler (B-3),
f) the intermediate dental filler (B-3) undergoes a heat treatment to terminate the reaction between the intermediate dental filler (B-3) and the compound (G) and so to obtain an intermediate filler (B-5),
g) the intermediate dental filler (B-5) is then mixed in a solvent medium with at least one compound (G) as defined above and in the presence of at least one dispersant (H) as defined above,
h) the solvent is removed by filtration to give an intermediate dental filler (B-6), and
i) the intermediate dental filler (B-6) undergoes a heat treatment to terminate the reaction between the intermediate dental filler (B-6) and the compound (G) and so to obtain a treated dental filler (B).

According to one preferred embodiment, the overall proportion of dental fillers (B) represents up to 85% by weight in relation to the total weight of the dental composition, and preferably between 60% and 80% by weight.

Advantageously the treatment of the dental filler (B) is implemented with up to 20% by weight, preferably between 1% and 15% by weight and more preferably between 2% and 10% by weight of the compound (G) in relation to the total weight of glass to be treated.

Advantageously the treatment of the dental filler (B) is implemented with up to 20% by weight, preferably between 0.01% and 10% by weight and more preferably between 0.1% and 1% by weight of the compound (H) in relation to the total weight of glass to be treated.

Advantageously the treatment of the dental filler (B) is implemented with up to 20% by weight, preferably between 1% and 15% by weight and more preferably between 2% and 10% by weight of the compound (F) in relation to the total weight of glass to be treated.

The organosilicon coupling agent (F) preferably has the following chemical formula:

in which formula:

R is a hydrogen or a C1-C4 linear or branched alkyl or alkenyl radical, $R^1$ is a linear or branched alkyl radical or a phenyl radical, x is 0, 1 or 2, and X being defined by the following formula:

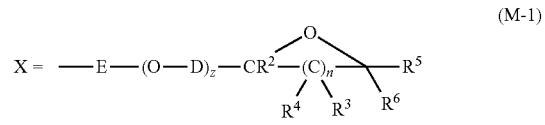

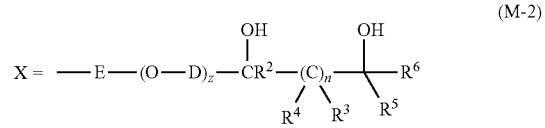

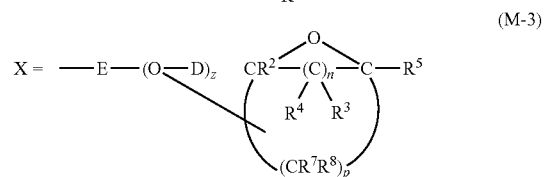

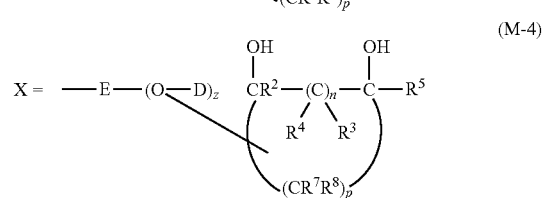

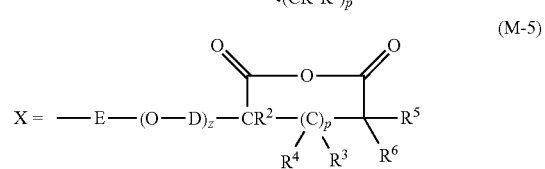

(M-6)

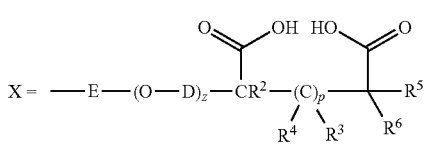

where:
E and D, which are identical or different radicals, are selected from C1-C12 linear or branched alkyls,
z is 0 or 1,
n is 0 or 1,
p is 0, 1, 2, 3, 4, 5 or 6;
$R^2$, $R^3$, $R^4$, $R^5$, $R^6$, $R^7$ and $R^8$ are identical or different radicals representing a hydrogen atom or a linear or branched $C_1$-$C_{12}$ alkyl.

Preferred organosilicon coupling agents (F) include the following compounds: glycidyloxypropyltrimethoxysilane, the product of hydrolysis of glycidyloxypropyltrimethoxysilane; glycidyloxypropyltriethoxysilane, the product of hydrolysis in acidic medium of glycidyloxypropyltriethoxysilane; glycidyloxypropyl-dimethoxymethylsilane or its hydrolysis product, the silane beta-(3,4-epoxycyclohexyl) ethyltriethyoxysilane or its hydrolysis product, the silane beta-(3,4-epoxycyclohexyl)ethyltrimethoxysilane or the product of hydrolysis.

The compound (G) is preferably a compound which is a monomer, an oligomer, an organic polymer or an organosiloxane containing at least one oxirane, oxetane, alkenyl ether and/or carbonate function and more preferably still containing at least one oxirane function.

More preferably still, the compound (G) contains at least one function selected from the group consisting of the following structures (M-7) to (M-12):

(M-7)

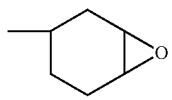

(M-8)

(M-9)

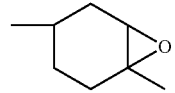

(M-10)

(M-11)
—$(CH_2)_3$—O—CH=$CH_2$;

(M-12)
—$(CH_2)_3$—O—CH=CH—R'' where R'' represents a linear or branched $C_1$-$C_6$ alkyl radical.

According to another preferred embodiment, the compound (G) is a silicone oligomer (G-1) or a silicone polymer (G-2). The silicone oligomer (G-1) and the silicone polymer (G-2) comprise:
a) at least one unit of formula:

(M-13)

in which formula:
a=0, 1 or 2,
$R^0$, identical or different at each occurrence, represents an alkyl, cycloalkyl, aryl, vinyl, hydrogeno or alkoxy radical, preferably a $C_1$-$C_6$ lower alkyl,
Z, identical or different at each occurrence, is an organic substituent containing at least one oxirane, alkenyl ether, oxetane and/or carbonate function, and
b) at least two silicon atoms.

Advantageously the silicone oligomer (G-1) and the silicone polymer (G-2) are selected from the group consisting of the compounds of formulae:

a)

(S-1)

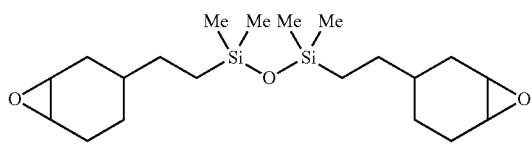

b)

(S-2)

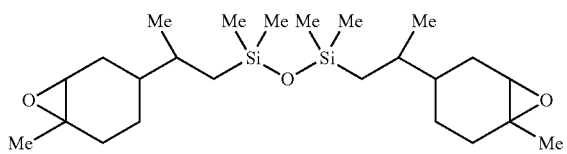

c)

(S-3)

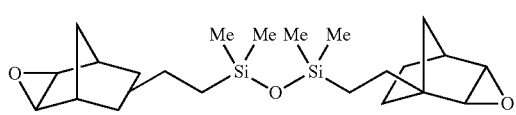

d)
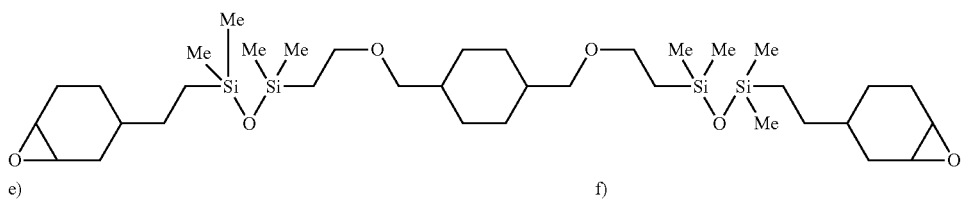
(S-4)
e)
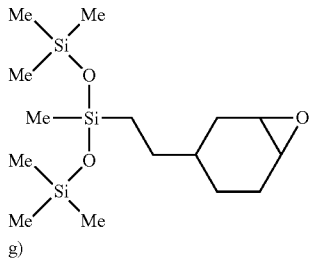
(S-5)
f)
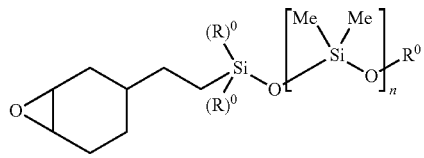
(S-6)
(n < 1000)
g)
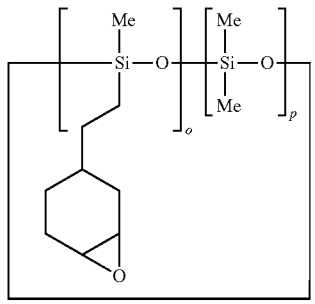
(S-7)
(o + p) < 10
o > 1
h)
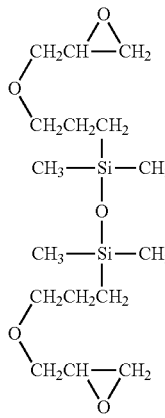
(S-8)
i)
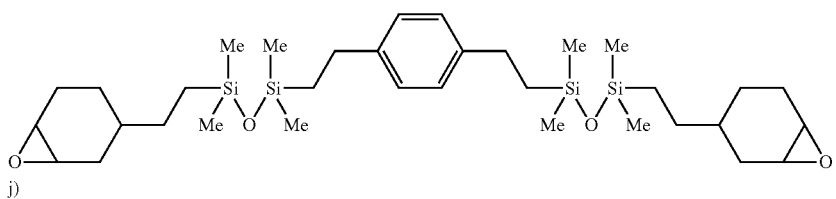
(S-9)
j)
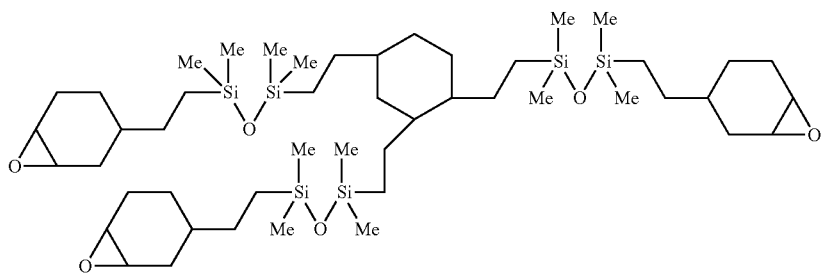
(S-10)
k)
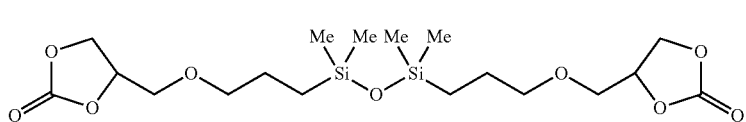
(S-11)

-continued
l)
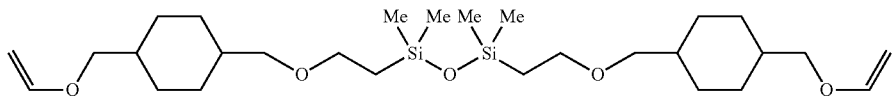
(S-12)
m)
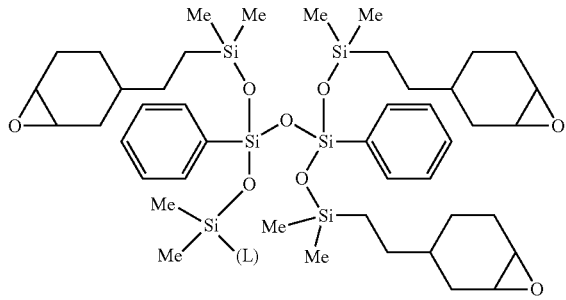
(S-13)
with L=H; OH; Me; phenyl; $C_1$-$C_{12}$ alkyl; $C_1$-$C_6$ cycloalkyl or the groups:
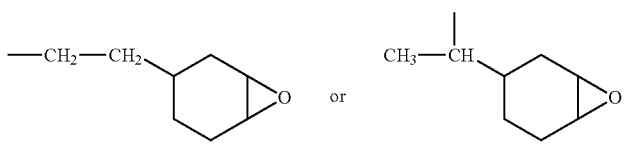
n)
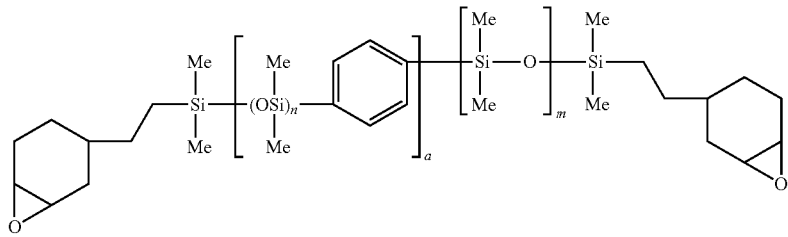
(S-14)
with n<100; a<100 and m<100
o)
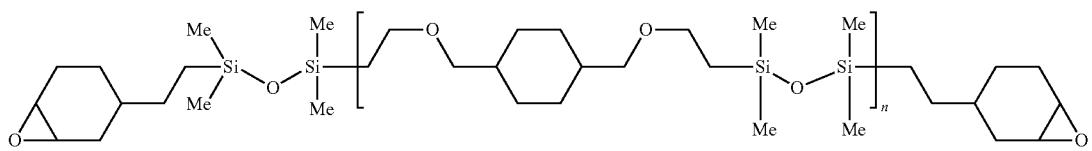
(S-15)
in which formulae the groups R, which are identical or different, represent an alkyl, cycloalkyl or aryl radical and preferably a $C_1$-$C_6$ lower alkyl.

(S-16)
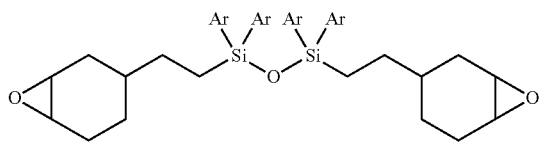
(S-17)
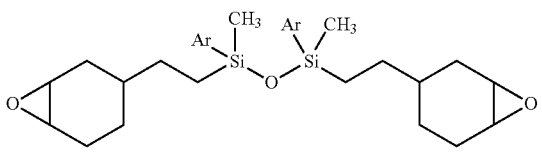
(S-18)
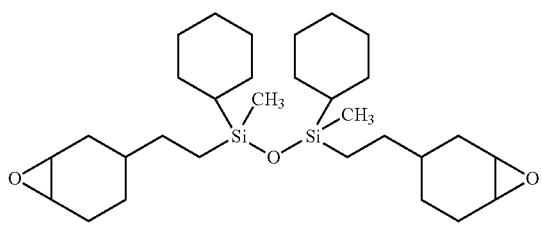
(S-19)
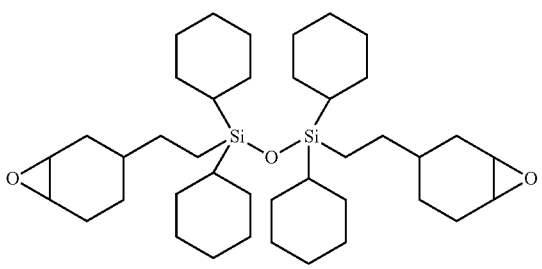
(S-20)
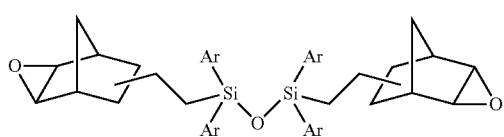
(S-21)
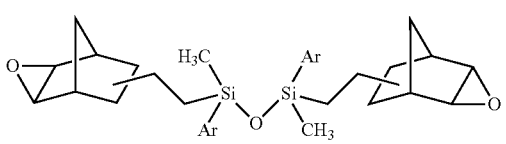
(S-22)
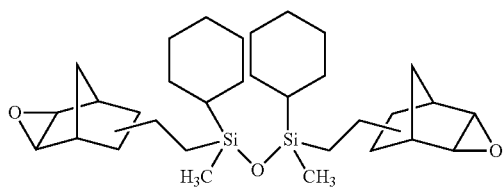
(S-23)
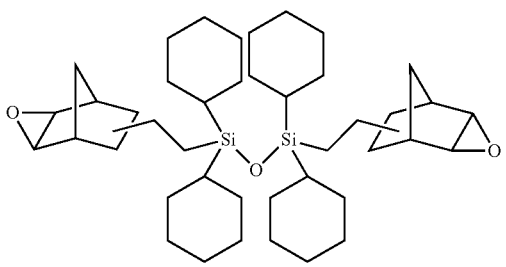
(S-24)
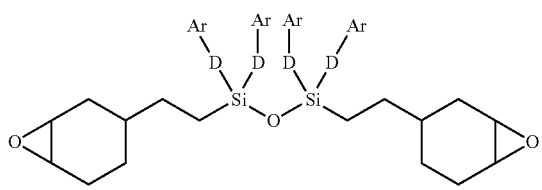
(S-25)
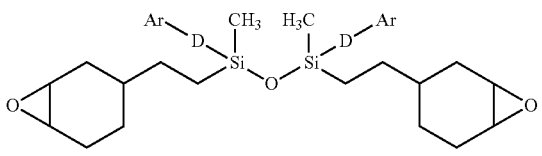
(S-26)
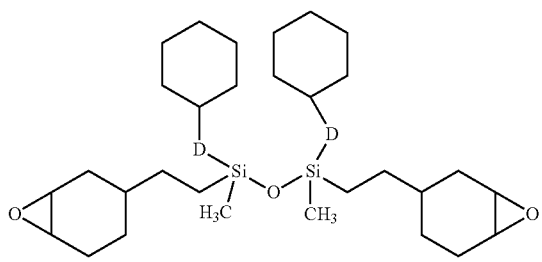
(S-27)
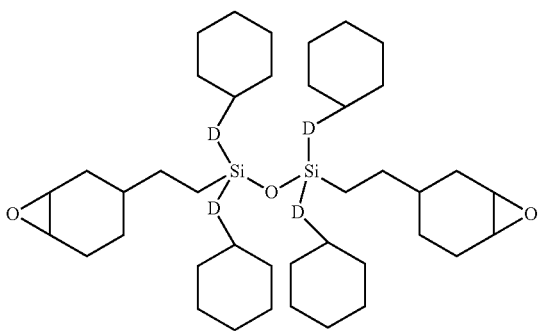
(S-28)
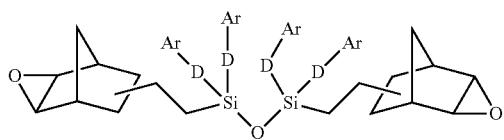
(S-29)
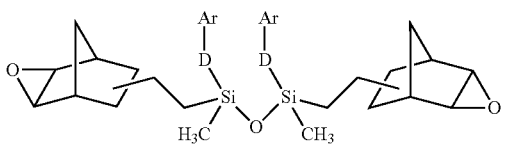

-continued
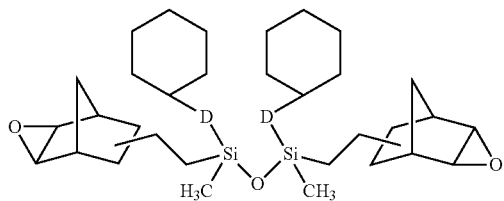
(S-30)
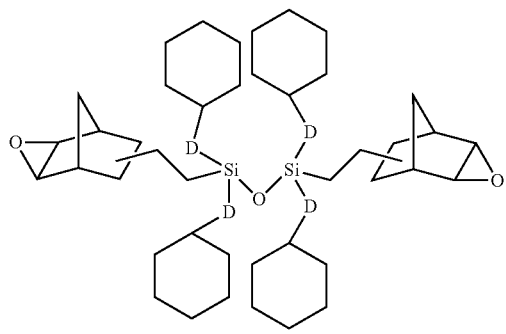
(S-31)
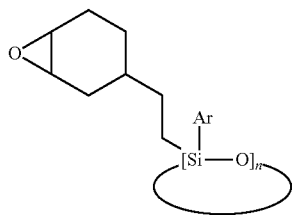
(S-32)
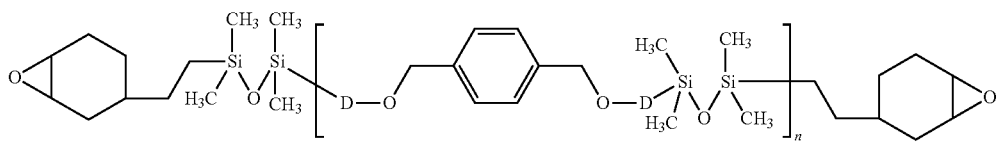
(S-33)
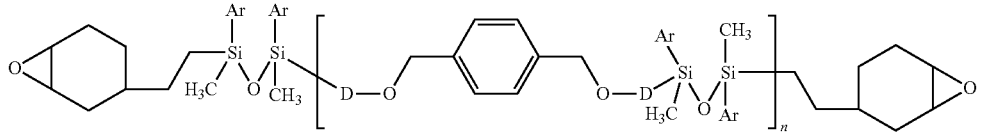
(S-34)
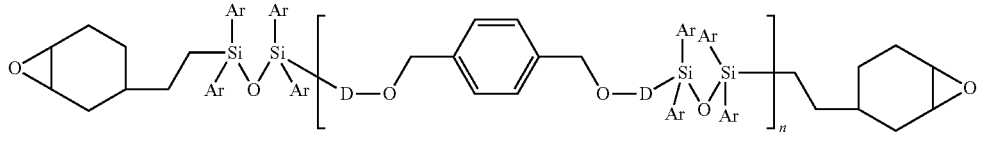
(S-35)
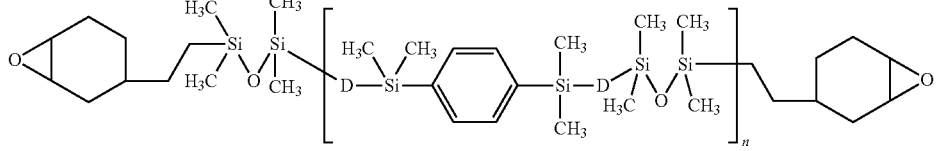
(S-36)
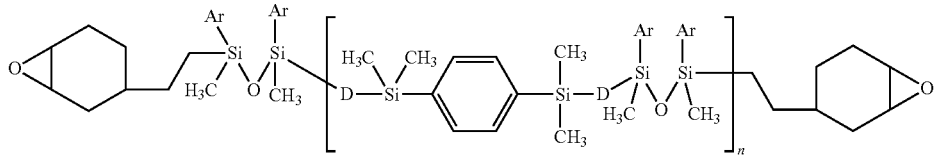
(S-37)
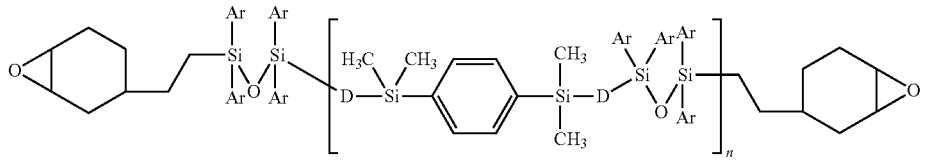
(S-38)

-continued
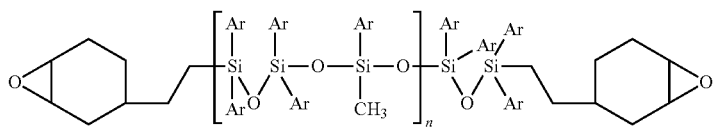 (S-39)
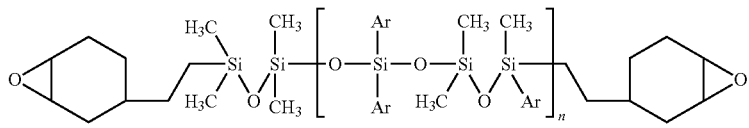 (S-40)
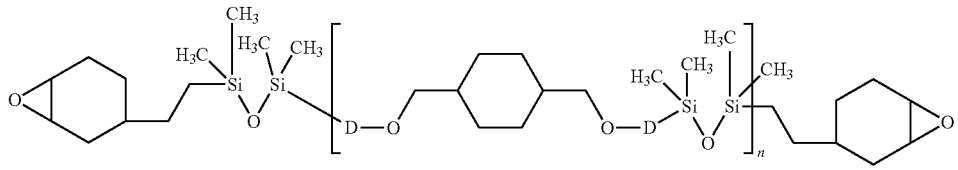 (S-41)
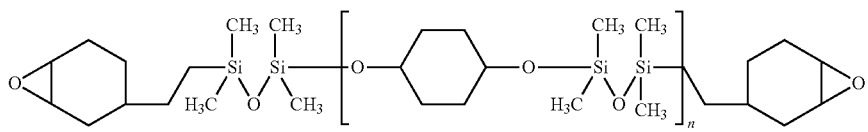 (S-42)
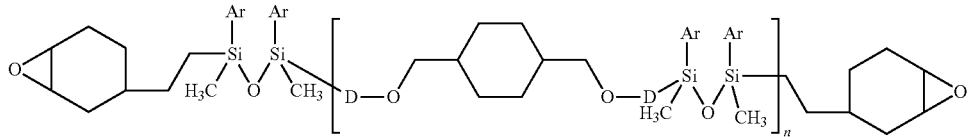 (S-43)
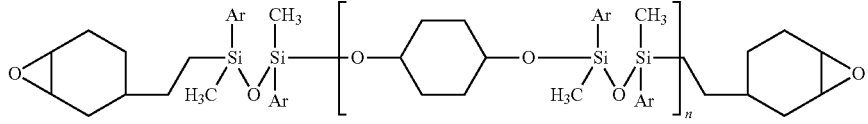 (S-44)
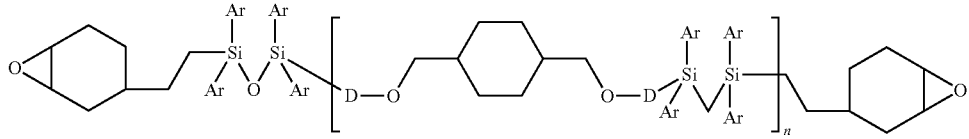 (S-45)
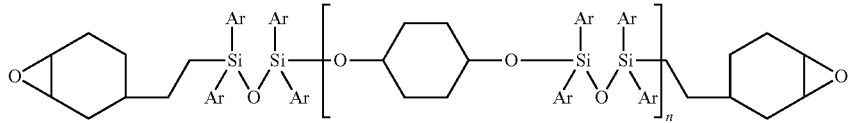 (S-46)
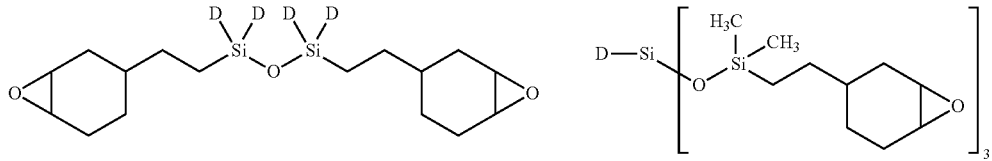 (S-47) (S-48)
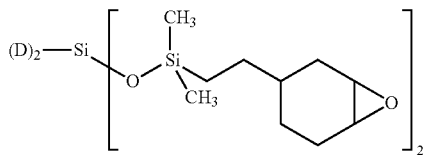 (S-49)
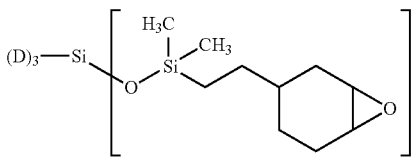 (S-50)

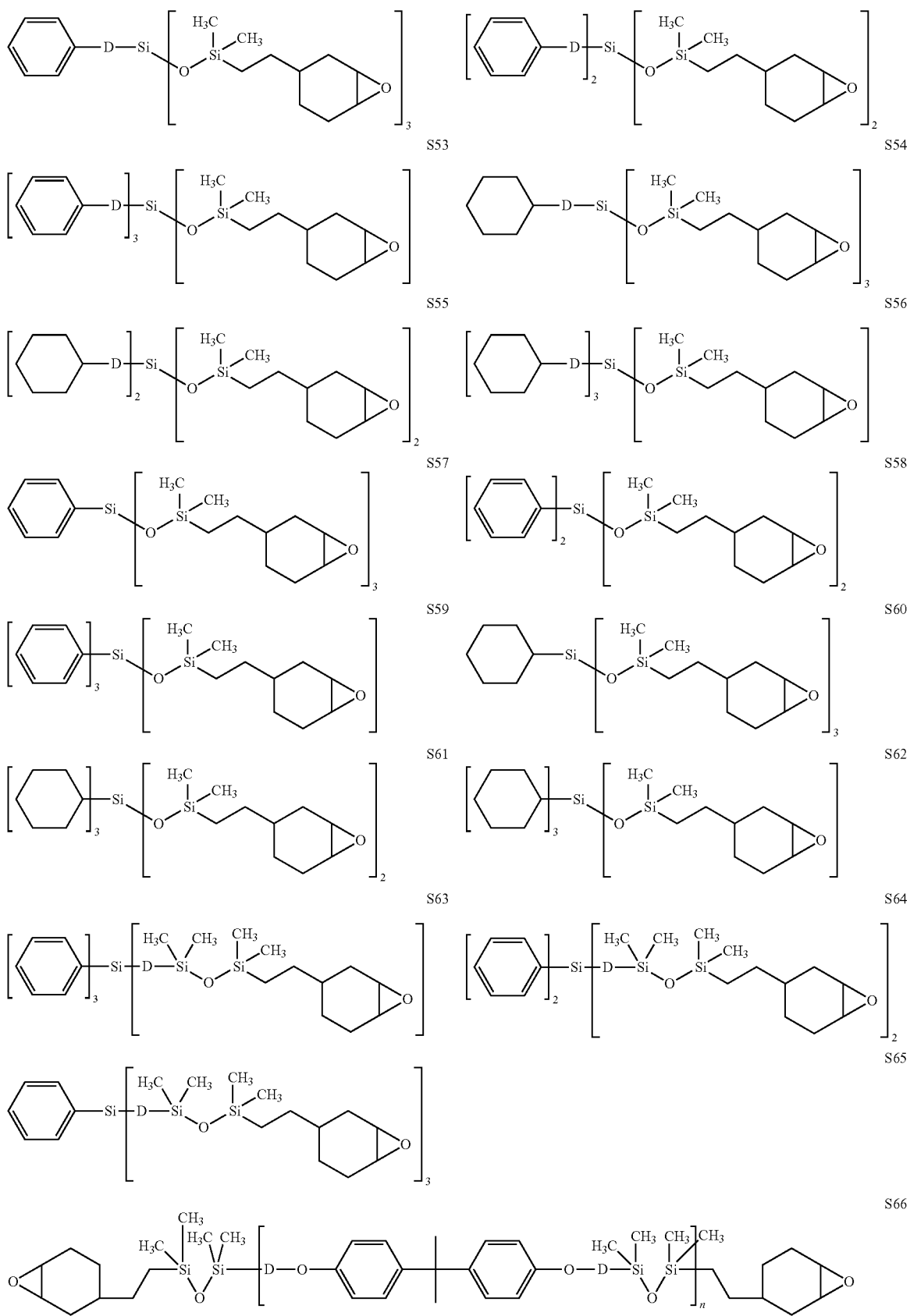

-continued
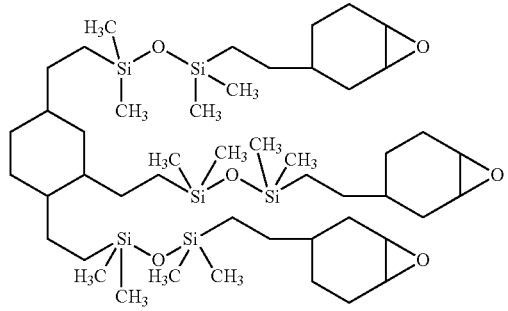
S67
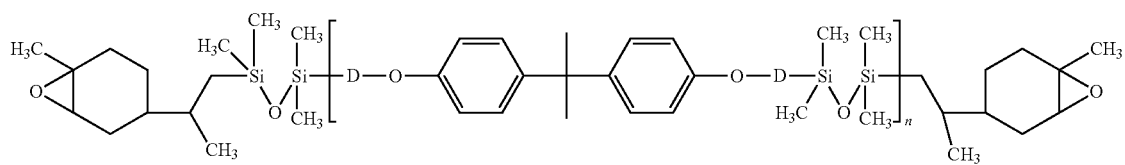
S68
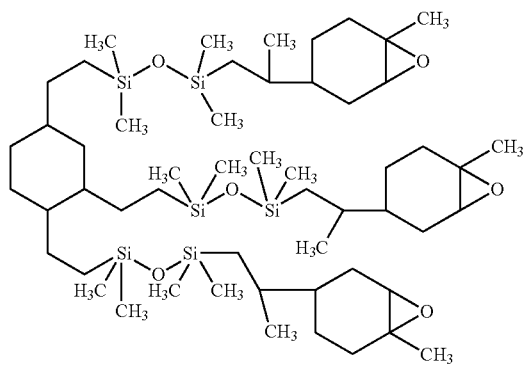
S69
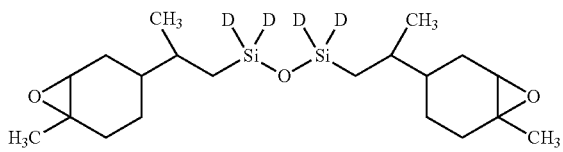
S70
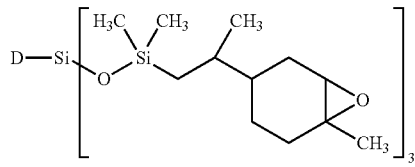
S71
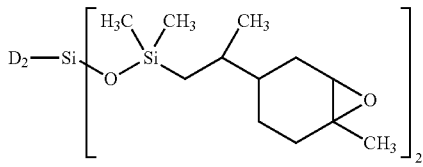
S72
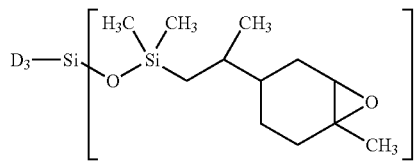
S73
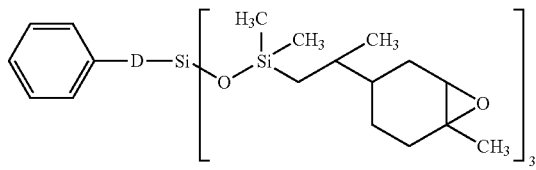
S74
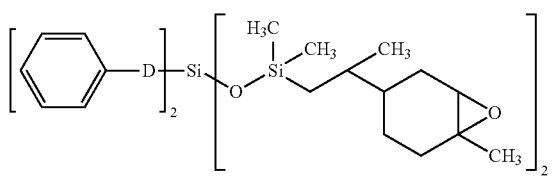
S75
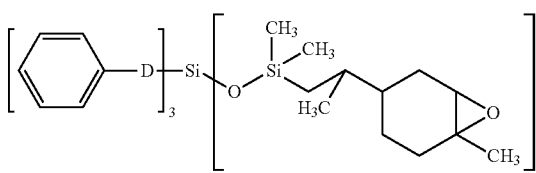
S76

-continued
S77
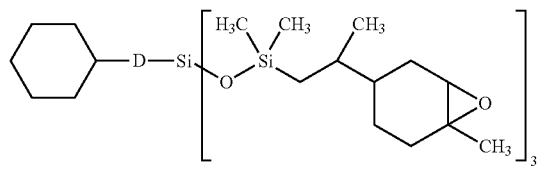
S78
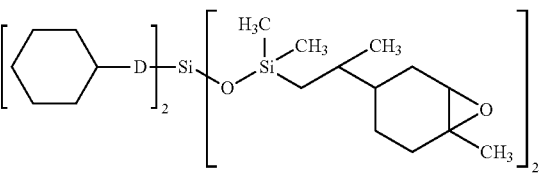
S79
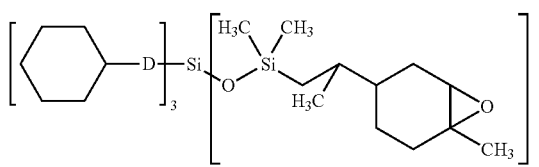
S80
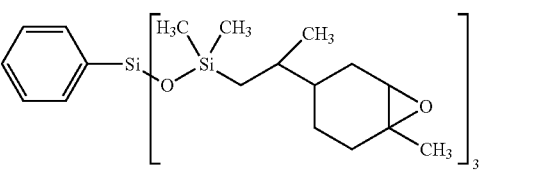
S81
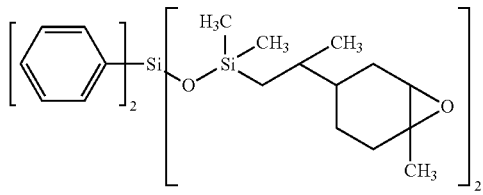
S82
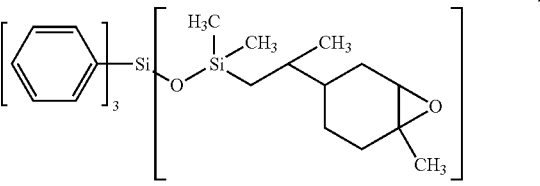
S83
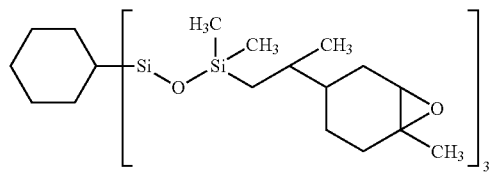
S84
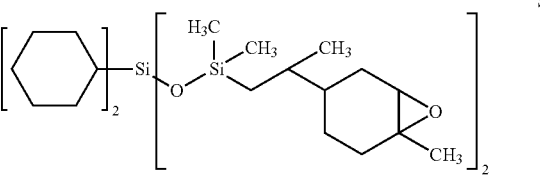
S85
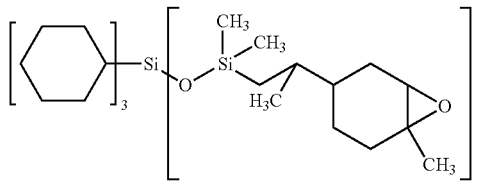
S86
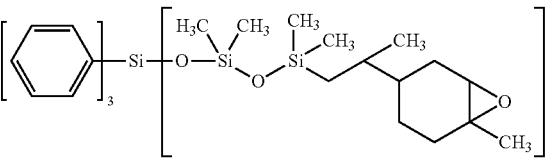
S87
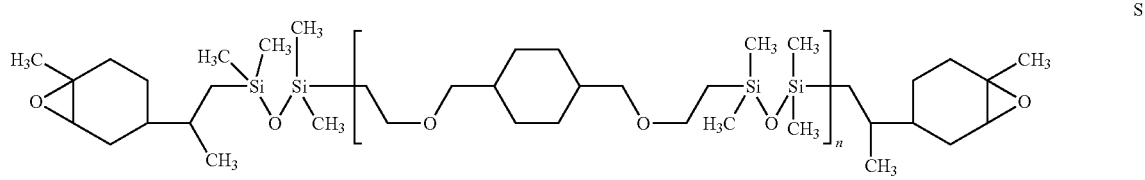
S88
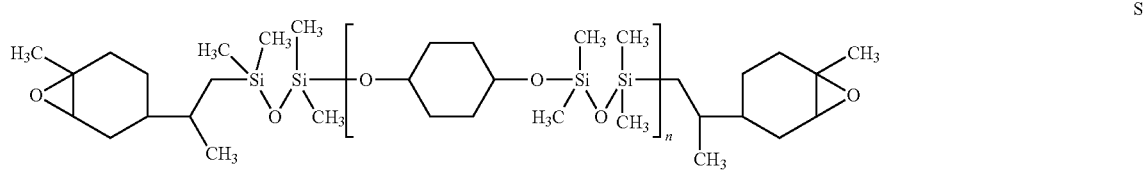
S89
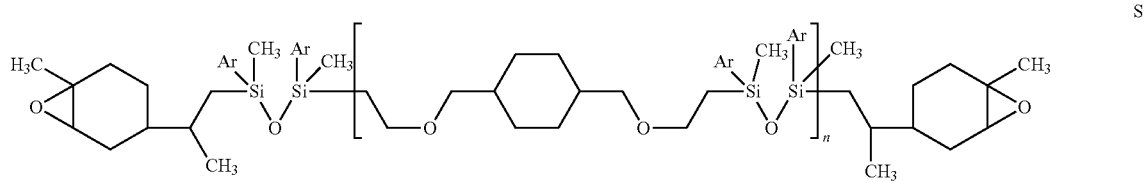

-continued

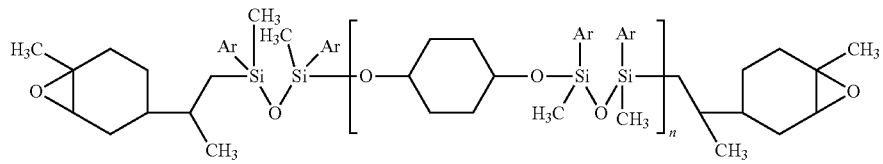
S90

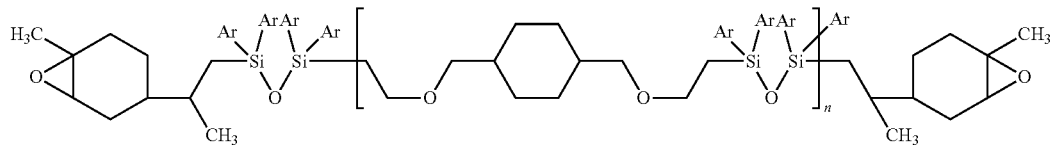
S91

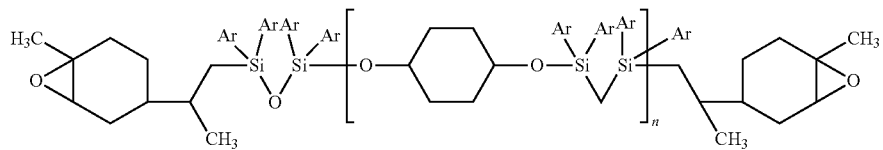
S92 in which formulae the group D is a linear or branched $C_1$-$C_{12}$ alkyl group and n is an integer between 1 and 20 (inclusive), with Ar=aryl group.

According to another preferred embodiment, the compound (G) is a silane (G-3) which is selected from the group consisting of the molecules (S-93) to (S-95):

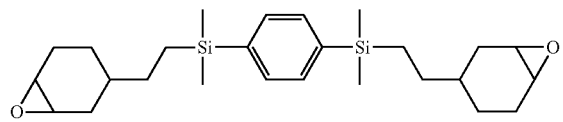
(S-93)

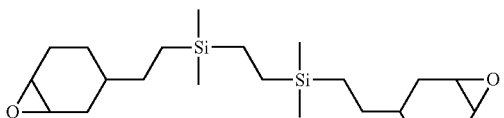
(S-94)

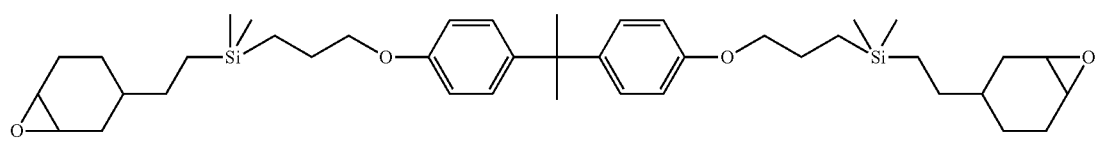
(S-95)

According to another preferred embodiment, the compound (G) is an organic compound (G-4) selected from the group consisting of the molecules (S-96) to (S-104):

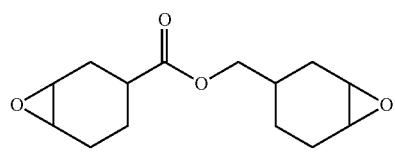
(S-96)

-continued

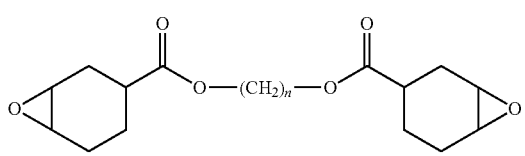
(S-97)

(S-98)

in which formulae: n is an integer between 1 and 10 (inclusive).

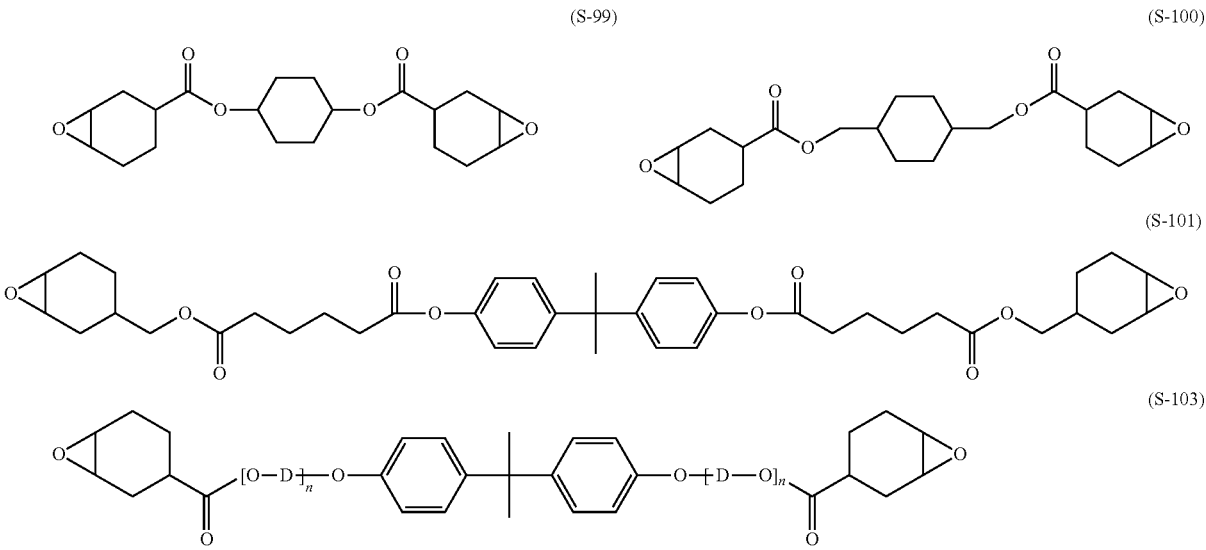

with n<100 and D=linear or branched $C_1$-$C_{12}$ alkyl.

Among the molecules of type (S-103) it is possible to select the resin UVR6150®, which is sold by Dow Chemical.

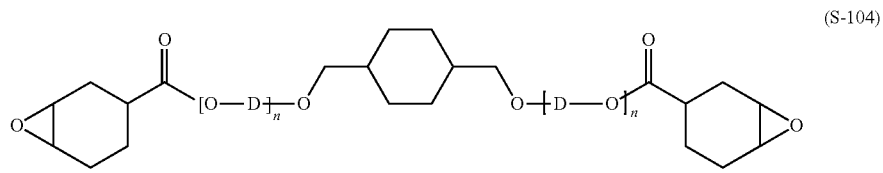

with n<100 and the group D=linear or branched $C_1$-$C_{12}$ alkyl.

For the resins of type (S-104), the one in which n=0 is particularly suitable for the invention.

Generally speaking, photochemical activation is performed under UV radiation. More particularly, a UV radiation is used whose wavelength is of the order of 200 to 500 nm for producing dental prostheses and a visible UV radiation with a wavelength of more than 400 nm is used for producing restoration materials. A wavelength greater than 400 nm allows crosslinking and/or polymerization in the oral environment.

Activation actinically (photochemically) may be advantageously supplemented (or even replaced) by thermal activation.

The cationically reactive compound (A) is preferably selected from the group of monomers and/or (co)polymers comprising:

epoxies, vinyl ethers, oxetanes, spiro-ortho-carbonates, spiro-orthoesters, and combinations thereof.

More preferably still, the cationically reactive compound (A) is a silicone oligomer (G-1), a silicone polymer (G-2), a silane (G-3), or an organic compound (G-4) as defined above by the unit (M-13), the molecules (S-1) to (S-101).

In the formula (M-13), the reactive functions Z that are of particular interest comprise at least one reactive function selected from the following radicals:

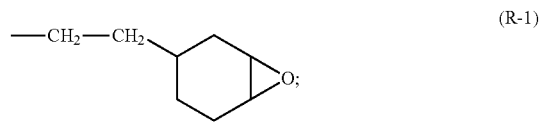
(R-1)

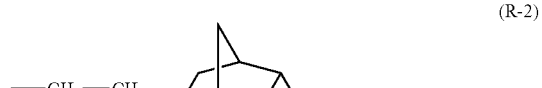
(R-2)

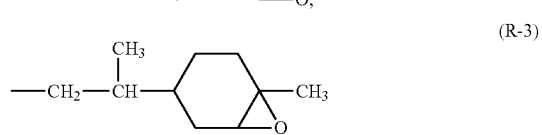
(R-3)

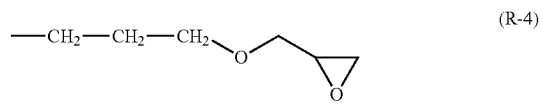
(R-4)

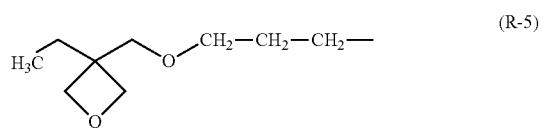
(R-5)

(R-6)

(R-7)

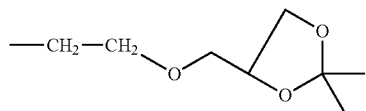

(R-8):

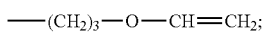

(R-9):

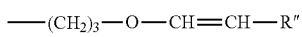

with R" representing a $C_1$-$C_6$ linear or branched alkyl radical.

According to one advantageous version, the cationically reactive compound (A) is combined with an organic epoxy resin or oxetane representing less than 80% by mass of the fraction. Among the functional organic resins, preference will be given to those whose mass percentage of reactive function is less than 20% and preferably less than 15%. This will produce a corresponding reduction in the volume contraction during polymerization.

Preference will be given to selecting the resins of formula (M-103) and (S-104):

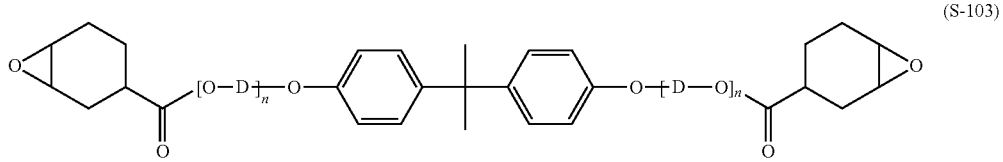

(S-103)

with n<100 and D=linear or branched C1-C12 alkyl.

Among the resins of type (S-103) it is possible to select the resin UVR6150®, which is sold by Dow Chemical.

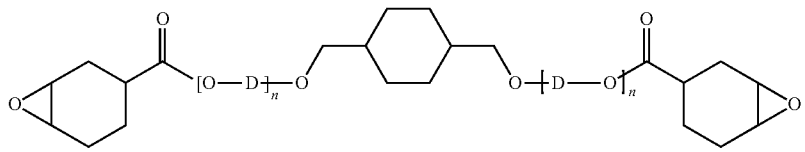

(S-104)

with n<100 and the group D=linear or branched $C_1$-$C_{12}$ alkyl.

For the resins of type (S-104), the one in which n=0 is particularly suitable for the invention.

Different types of dental fillers (B) and (B') can be used for preparing the compositions according to the invention. The fillers are selected as a function of the end use of the dental composition: they affect important properties such as appearance, penetration of UV radiation, and also mechanical and physical properties of the material obtained after crosslinking and/or polymerization of the dental composition.

As a reinforcing filler, use may be made of untreated or treated pyrogenic silica fillers, amorphous silica fillers, quartz, glasses or nonvitreous fillers based on oxides of silicon, of the type for example of those described in U.S. Pat. No. 6,297,181 (without barium), of zirconium, of barium, of strontium, of calcium, of fluorine, of aluminum, of titanium or of zinc, borosilicates, aluminosilicates, talc, Spherosils, ytterbium trifluoride, fillers based on polymers in the form of ground powder, such as inert or functionalized polymethyl methacrylates, or polyepoxides or polycarbonates, whiskers of ceramics (Si—C, Si—O—C, Si—N, Si—N—C, Si—N—C—O), or glass fibers.

The following are cited by way of example:
inert fillers based on polymethyl methacrylate LUXAS-ELF®, from the company UGL, which can be used in the dental field and are pigmented pink,
polydimethylsiloxane- or hexamethyldisilazane-treated fumed silica fillers with a specific surface area of 200 $m^2/g$,
untreated fumed silica fillers (Aerosil-AE200®, sold by the company Degussa), and
quartzes or glasses based on silicon oxides (Schott dental fillers GM27884, G018-066, and G018-163, sold by the company Schott).

According to one preferred embodiment of the invention, the dental filler (B) is an inorganic glass or a fumed silica.

In accordance with one advantageous feature of the invention, the dental fillers (B) represent up to 85% by weight, preferably between 50 and 85% by weight, and more preferably between 60 and 85% by weight, relative to the total weight of the dental composition.

For example, the dispersant (C) is selected from the group consisting of the following:
polyurethane/acrylate copolymers optionally converted to an alkylammonium salt form, acrylic copolymers optionally converted to an alkylammonium salt form, monodiesters of carboxylic acids, polyesters, polyethers, polyurethanes, modified polyurethanes, polyacrylate polyols, copolymers thereof or mixtures thereof. The dispersants sold under the brand name Disperbyk® (from the company Byk) or Solsperse® (from the company Avecia) are particularly suitable for the invention. Mention may be made, in particular and by way of example, of the following commercial products: Disperbyk® 164, Disperbyk® 161, Disperby0166, Disperby02070, Disperbyk® 9075, and Disperbyk® 9076. Mention may also be made of the dispersants cited in the following patents:
U.S. Pat. No. 5,882,393, describing dispersants based on polyurethane/imidazole acrylates or epoxides;
U.S. Pat. No. 5,425,900, describing dispersants based on polyurethanes;
U.S. Pat. No. 4,795,796, describing dispersants based on polyurethane/polyoxyalkylene glycol monoalkyl ethers;
patent application WO-A-99/56864, describing dispersants based on polyurethane/poly(oxy-alkylenecarbonyl)s: derived from ε-caprolactone and from δ-valerolactone; and
patent EP-B-0 403 197, describing grafted polyacrylate polyol dispersants comprising a random polyurethane/polyvinyl/polyacrylate copolymer and a polyoxyalkylene polyether.

Quantitatively speaking, the dispersant (C) may be present in the dental composition in a proportion of 50 ppm to 1%, preferably 100 ppm to 5000 ppm. The amine index of the dispersant (C) is preferably less than or equal to 60 and more preferably between 0.1 and 50 mg of potassium hydroxide per gram of dispersant (C). The acid index of the dispersant is advantageously less than or equal to 200, preferably less than or equal to 100, and more preferably between 1 and 60 mg of potassium hydroxide per gram of dispersant.

The cationic photoinitiators (D) are selected from the onium borates (taken individually or in a mixture) of an element from groups 15 to 17 of the Periodic Table [Chem. & Eng. News, Vol. 63, No. 5, 26, dated Feb. 4, 1985] or of an organometallic complex of an element from groups 4 to 10 of the Periodic Table [same reference].

According to one preferential embodiment the cationic photoinitiator (D) is of borate type and is selected from those for which:

a) the cationic entity of the borate is selected from:
(1) onium salts of formula:

$$[(R^9)_n\text{-}A\text{-}(R^{10})_m]^+ \qquad (I)$$

in which:
A represents an element from groups 15 to 17 such as, for example: I, S, Se, P or N,
$R^9$ represents a C6-C20 heterocyclic or carbocyclic aryl radical, it being possible for said heterocyclic radical to contain nitrogen or sulfur as heteroelements,
$R^{10}$ represents $R^9$ or a C1-C30 linear or branched alkyl or alkenyl radical, said radicals $R^9$ and $R^{10}$ being optionally substituted by a C1-C25 alkoxy, C1-C25 alkyl, nitro, chloro, bromo, cyano, carboxyl, ester or mercapto group,
m and n are integers, with n+m=v+1, v being the valence of the element A,
(2) oxoisothiochromanium salts, specifically those described in patent application WO 90/11303, particularly the sulfonium salt of 2-ethyl-4-oxoisothiochromanium or of 2-dodecyl-4-oxoisothiochromanium, and the oxoisothiochromanium salts of structural formula V:

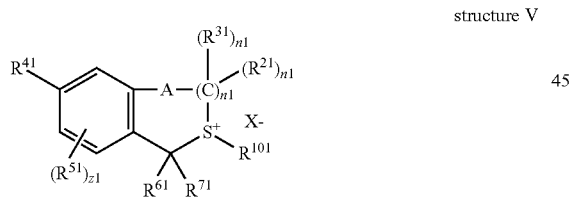
structure V in which:
A represents

n1=an integer between 1 and 3;
z1=an integer between 0 and 3;
X represents a group of formula $M^1Y^1_{r1}$ (1) or of formula $Q^1$ (2),
where:
$M^1$=Sb, As, P, B or Cl,
$Y^1$ represents a halogen (preferably F or Cl) or O, and r1 is an integer between 4 and 6, $Q^1$ represents a sulfonic acid $R^{81}$—$SO_3$ where $R^{81}$ is an alkyl or aryl group, or an alkyl or aryl group substituted by a halogen, preferably F or Cl,
$R^{101}$ represents an alkyl or a cycloalkyl group, preferably $C_1$-$C_{20}$, or an aryl group,
$R^{21}$ represents a hydrogen, an alkyl, alkenyl, cycloalkenyl or cycloalkyl group, preferably $C_1$-$C_{20}$, or an aryl group, all of the $R^{21}$s being independent of one another,
$R^{31}$ represents a hydrogen, an alkyl, alkenyl, cycloalkenyl or cycloalkyl group, preferably $C_1$-$C_{20}$, or an aryl group, all of the $R^{31}$s being independent of one another,
$R^{41}$ represents a hydrogen, halogen, an alkenyl group, vinyl for example, or a cycloalkenyl, alkyl, or cycloalkyl group, preferably $C_1$-$C_{20}$, an alkoxy or thioalkoxy group, preferably $C_1$-$C_{20}$, a poly(alkylene oxide) group having up to 10 alkylene oxide units and terminated by a hydroxyl or an alkyl ($C_1$-$C_{12}$), or an aryl group, or an aryloxy or thioaryloxy group,
$R^{51}$ represents a halogen, an alkenyl group, vinyl for example, or a cycloalkenyl, alkyl, or cycloalkyl group, preferably $C_1$-$C_{20}$, an alkoxy or thioalkoxy group, preferably $C_1$-$C_{20}$, a poly(alkylene oxide) group having up to 10 alkylene oxide units and terminated by a hydroxyl or an alkyl ($C_1$-$C_{12}$), or an aryl group, or an aryloxy or thioaryloxy group,
$R^{61}$ represents a hydrogen, an alkyl, alkenyl, cycloalkenyl or cycloalkyl group, preferably $C_1$-$C_{20}$, or an aryl group,
$R^{71}$ represents a hydrogen, an alkyl, alkenyl, cycloalkenyl or cycloalkyl group, preferably $C_1$-$C_{20}$, or an aryl group; and (3) organometallic salts of the following formula:

$$(L_1L_2L_3M)^{+q} \qquad (II)$$

in which:
M represents a metal from group 4 to 10, especially iron, manganese, chromium or cobalt,
L1 represents 1 ligand bonded to the metal M by π electrons, the ligand being selected from $\eta^3$-alkyl, $\eta^5$-cyclopentadienyl and $\eta^7$-cycloheptatrienyl ligands and the $\eta^6$-aromatic compounds selected from optionally substituted $\eta^6$-benzene ligands and compounds having 2 to 4 fused rings, each ring being capable of contributing to the valence layer of the metal M via 3 to 8 π electrons,
L2 represents a ligand bonded to the metal M by π electrons, the ligand being selected from $\eta^7$-cycloheptatrienyl ligands and the $\eta^6$-aromatic compounds selected from optionally substituted $\eta^6$-benzene ligands and compounds having 2 to 4 fused rings, each ring being capable of contributing to the valence layer of the metal M via 6 or 7 π electrons,
L3 represents 0 to 3 identical or different ligands bonded to the metal M by a electrons, the ligand(s) being selected from CO and NO2+; the total electronic charge q of the complex to which L1, L2 and L3 contribute, and the ionic charge of the metal M, being positive and being 1 or 2; and b) cationic photoinitiators (D) in which the anionic borate entity has the formula:

$$[BX_aR_b]^- \qquad (III)$$

in which formula:
a and b are integers ranging from 0 to 3 for a and from 1 to 4 for b, with a+b=4,
the symbols X represent:
a halogen (chlorine, fluorine) atom, with a=0 to 3, or an OH function, with a=0 to 2,
the symbols R are identical or different and represent:
a phenyl radical substituted by at least one electron-withdrawing group such as, for example, $OCF_3$, $CF_3$, $NO_2$ or CN and/or by at least two halogen atoms (especially fluorine), when the cationic entity is an onium of an element from groups 15 to 17,
a phenyl radical substituted by at least one electron-withdrawing element or group, in particular a halogen atom (especially fluorine), $CF_3$, $OCF_3$, $NO_2$ or CN, when the cationic entity is an organometallic complex of an element from groups 4 to 10, or
an aryl radical containing at least two aromatic nuclei, such as, for example, biphenyl, naphthyl, optionally substituted by at least one electron-withdrawing element or group, in particular a halogen atom, especially fluorine, $OCF_3$, $CF_3$, $NO_2$ or CN, irrespective of the cationic entity.

Without any limitative effect, there now follow further details regarding the subclasses of onium borate and of organometallic-salt borate that are more particularly preferred in the context of the use in accordance with the invention.

According to one preferred version of the invention the especially suitable species of the anionic borate entity are the following:

| | |
|---|---|
| 1': | $[B(C_6F_5)_4]^-$ |
| 2': | $[(C_6F_5)_2BF_2]^-$ |
| 3': | $[B(C_6H_4CF_3)_4]^-$ |
| 4': | $[B(C_6F_4OCF_3)_4]^-$ |
| 5': | $[B(C_6H_3(CF_3)_2)_4]^-$ |
| 6': | $[B(C_6H_3F_2)_4]^-$ |
| 7': | $[C_6F_5BF_3]^-$ |

According to another preferred version of the invention the onium salts of formula (S-26) that can be used are described in numerous documents, and particularly in U.S. Pat. No. 4,026,705, U.S. Pat. No. 4,032,673, U.S. Pat. No. 4,069,056, U.S. Pat. No. 4,136,102, and U.S. Pat. No. 4,173,476. Among these salts, particular privilege will be given to the following cations:

$[(C_8H_{17})—O—(C_6H_4)—I—C_6H_5)]^+$; $[C_{12}H_{25}—(C_6H_4)—I—C_6H_5]^+$; $[(C_8H_{17}—O—(C_6H_4))_2I]^+$
$[(C_8H_{17})—O—(C_6H_4)—I—C_6H_5)]^+$; $[(C_6H_5)_2S—(C_6H_4)—O—C_8H_{17}]^+$; $[CH_3—C_6H_4—I—C_6H_4—CH_2CH(CH_3)_2]^+$;
$[(C_{12}H_{25}—(C_6H_4)—I—(C_6H_4)—CH—(CH_3)_2]^+$;
$[(C_{12}H_{25}—C_6H_4)_2I]^+$; $[(C_6H_5)_3S]^+$;
$[CH_3—(C_6H_4)—I—(C_6H_4)—CH(CH_3)_2]^+$
$(\eta 5\text{-cyclopentadienyl})(\eta 6\text{-toluene})Fe^+$;
$(\eta 5\text{-cyclopentadienyl})(\eta 6\text{-cumene})Fe^+$,
$(\eta 5\text{-cyclopentadienyl})(\eta 6\text{-1-methylnaphthalene})Fe^+$;
$[(C_6H_5)—S—C_6H_4—S—(C_6H_5)_2]^+$; $[(CH_3—(C_6H_4)—I—(C_6H_4)—OC_2H_5]^+$; $[(C_nH_{2n+1}—C_6H_4)_2I]^+$ (with, for the group $C_nH_{2n+1}$, n=1 to 18 and is linear or branched).

According to another preferred version, the organometallic salts (3) of formula (S-27) that can be used are described in documents U.S. Pat. No. 4,973,722, U.S. Pat. No. 4,992,572, EP-A-203 829, EP-A-323 584, and EP-A-354 181. The organometallic salts more readily employed according to the invention are in particular:

$(\eta^5\text{-cyclopentadienyl})(\eta^6\text{-toluene})Fe^+$,
$(\eta^5\text{-cyclopentadienyl})(\eta^6\text{-1-methylnaphthalene})Fe^+$,
$(\eta^5\text{-cyclopentadienyl})(\eta^6\text{-cumene})Fe^+$,
$bis(\eta^6\text{-mesitylene})Fe^+$,
$bis(\eta^6\text{-benzene})Cr^+$.

In accordance with these preferred versions mention may be made, as examples of onium borate photoinitiators, of the following products:
(P-16): $[(C_8H_{17})—O—C_6H_4—I—C_6H_5)]^+$, $[B(C_6F_5)_4]^-$;
(P-17): $[C_{12}H_{25}—C_6H_4—I—C_6H_5]^+$, $[B(C_6F_5)_4]^-$;
(P-18): $[(C_8H_{17}—O—C_6H_4)_2I]^+$, $[B(C_6F_5)_4]^-$;
(P-19): $[(C_8H_{17})—O—C_6H_4—I—C_6H_5)]^+$, $[B(C_6F_5)_4]^-$;
(P-20): $[(C_6H_5)_2S—C_6H_4—O—C_8H_{17}]^+$, $[B(C_6H_4CF_3)_4]^-$;
(P-21): $[(C_{12}H_{25}—C_6H_4)_2I]^+$, $[B(C_6F_5)_4]^-$;
(P-22): $[(CH_3—C_6H_4—I—C_6H_4—CH(CH_3)_2]^+$, $[B(C_6F_5)_4]^-$;
(P-23): $(\eta 5\text{-cyclopentadienyl})(\eta 6\text{-toluene})Fe^+$, $[B(C_6F_5)_4]^-$;
(P-24): $(\eta 5\text{-cyclopentadienyl})(\eta 6\text{-1-methylnaphthalene})Fe^+$, $[B(C_6F_5)_4]^-$;
(P-25): $(\eta 5\text{-cyclopentadienyl})(\eta 6\text{-cumene})Fe^+$, $[B(C_6F_5)_4]^-$;
(P-26): $[(C_{12}H_{25}—C_6H_4)_2I]^+$, $[B(C_6H_3(CF_3)_2]^-$;
(P-27): $[CH_3—C_6H_4—I—C_6H_4—CH_2CH(CH_3)_2]^+$, $[B(C_6F_5)_4]^-$;
(P-28): $[CH_3—C_6H_4—I—C_6H_4—CH_2CH(CH_3)_2]^+$, $[B(C_6H_3(CF_3)_2)_4]^-$; and
(P-29): $[CH_3—C_6H_4—I—C_6H_4—CH(CH_3)_2]^+$, $[B(C_6H_3(CH_3)_2)_4]^-$.

As a further reference from the literature for defining the onium borates (1) and (2) and the organometallic-salt borates (3), mention may be made of the entirety of the content of patent applications EP-A-0 562 897 and EP-A-0 562 922. This content is integrally incorporated by reference in the present disclosure.

As a further example of onium salt which can be used as photoinitiator, mention may be made of those disclosed in U.S. Pat. Nos. 4,138,255 and 4,310,469. Use may also be made of other cationic photoinitiators, for example:
hexafluorophosphate or hexafluoroantimonate iodonium salts, such as:
$[CH_3—[(C_6H_4)—I—[(C_6H_4)—CH(CH_3)_2]^+$, $[PF_6]^-$;
$[CH_3—(C_6H_4)—I—(C_6H_4)—CH_2CH(CH_3)_2]^+$, $[PF_6]^-$;
$[(C_{12}H_{25}—C_6H_4)_2I]^+$, $[PF_6]^-$; or
the ferrocenium salts of these various anions.

The photosensitizer present within the dental composition according to the invention may be very varied in nature. In the context of the invention it corresponds in particular to one of the following formulae (IV) to (XXIV):

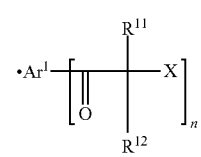

formula (IV)

in which n=1 or 2:
when n=1, $Ar^1$ represents an aryl radical containing 6 to 18 carbon atoms, a tetrahydronaphthyl, thienyl, pyridyl or furyl radical or a phenyl radical which carries one or more substituents selected from the group consisting of F, Cl, Br, CN, OH, linear or branched $C_1$-$C_{12}$ alkyls, —$CF^3$, —$OR^6$, —O-phenyl, —$SR''$, —S-phenyl, —SO$_2$-phenyl, —COOR$^{13}$, —O—(CH$_2$—CH═CH$_2$), —O(CH$_2$H$_4$—O)$_m$—H, —O(C$_3$H$_8$O)$_m$—H, m being between 1 and 100, when n=2, Ar$^1$ represents a C$_6$-C$_{12}$ arylene radical or a phenylene-T-phenylene radical in which T represents —O—, —S—, —SO$_2$— or —CH$_2$—, X represents a group —OR$^{14}$ or —OSiR$^{15}$ (R$^{16}$)$_2$ or together with R$^{11}$ forms a group —O—CH(R$^{17}$)—, R$^{11}$ represents a linear or branched C$_1$-C$_8$ alkyl radical which is unsubstituted or carries an OH, —OR$^{13}$, C$_2$-C$_8$ acyloxy, —CF$^3$ or —CN group, a C$_3$ or C$_4$ alkenyl radical, a C$_6$-C$_{18}$ aryl radical or a C$_7$ to C$_9$ phenylalkyl radical, R$^{12}$ has one of the meanings given for R$^{11}$ or represents a radical —CH$_2$CH$_2$R$^{18}$, or else together with R$^{11}$ forms a C$_2$-C$_8$ alkylene radical or a C$_3$-C$_9$ oxaalkylene or azaalkylene radical, R$^{13}$ represents a lower alkyl radical containing 1 to 12 carbon atoms, R$^{14}$ represents a hydrogen atom, a C$_1$-C$_{12}$ alkyl radical, a C$_2$-C$_6$ alkyl radical which carries an —OH, —OR$^{13}$ or CN group, a C$_3$-C$_6$ alkenyl radical, a cyclohexyl or benzyl radical, a phenyl radical optionally substituted by a chlorine atom or a linear or branched C$_1$-C$_{12}$ alkyl radical or a 2-tetrahydropyranyl radical, R$^{15}$ and R$^{16}$ are identical or different and each represent a C$_1$-C$_4$ alkyl radical or a phenyl radical, R$^{17}$ represents a hydrogen atom, a C$_1$-C$_8$ alkyl radical or a phenyl radical, R$^{18}$ represents a radical —CONH$_2$, —CONHR$^{13}$, —CON(R$^{13}$)$_2$, —P(O)(OR$^{13}$)$_2$ or 2-pyridyl;

formula (V)

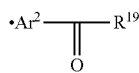

in which:

Ar$^2$ has the same meaning as Ar$^1$ in the formula (IV) in the case where n=1, R$^{19}$ represents a radical selected from the group consisting of a radical Ar$^2$, a linear or branched C$_1$-C$_{12}$ alkyl radical, a C$_6$-C$_{12}$ cycloalkyl radical and a cycloalkyl radical forming a C$_6$-C$_{12}$ ring with the carbon of the ketone or a carbon of the radical Ar$^2$, it being possible for these radicals to be substituted by one or more substituents selected from the group consisting of —F, —Cl, —Br, —CN, —OH, —CF$_3$, —OR$^{13}$, —SR$^{13}$, —COOR$^{13}$, linear or branched C$_1$-C$_{12}$ alkyl radicals which optionally carry an —OH, —OR$^{13}$ and/or —CN group, and linear or branched C$_1$-C$_8$ alkenyl radicals;

formula (VI)

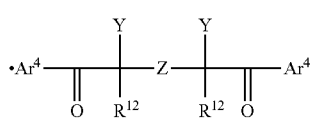

in which:

R$^{12}$, identical or different at each occurrence, has the same meaning as in formula (IV), Y, identical or different at each occurrence, represents X and/or R$^4$, Z represents:

a direct bond, a divalent C$_1$-C$_6$ alkylene radical, or a phenylene, diphenylene or phenylene-T-phenylene radical (T: linear or branched C$_1$-C$_{12}$ alkyl), or else forms, together with the two substituents R$^{12}$ and the two carbon atoms which carry these substituents, a cyclopentane or cyclohexane nucleus, a divalent group —O—R$^{19}$—O—, —O—SiR$^{15}$R$^{16}$—O—SiR$^{15}$R$^{16}$—O—, or —O—SiR$^{15}$R$^{16}$—O—, R$^{20}$ represents a C$_2$-C$_8$ alkylene, a C$_4$-C$_6$ alkenylene or xylylene radical, or else the entity:

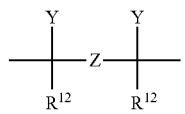

corresponds to —O—O— and Ar$^4$ has the same meaning as Ar$^1$ in the formula (IV) in the case where n=1.

class of the thioxanthones of formula (VII):

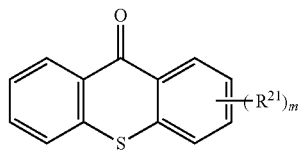

m=0 to 8,

R$^{21}$, identical or different substituent(s) on the aromatic ring(s), represent a linear or branched C$_1$-C$_{12}$ alkyl radical, a C$_6$-C$_{12}$ cycloalkyl radical, a radical Ar$^1$, a halogen atom or an —OH, —OR$^{13}$, —CN, —NO$_2$, —COOR$^{13}$, —OCOR$^{13}$, —N(R$^{13}$)$_2$, —O—R$^{13}$-(NR$^{13}$)$_2$, —CHO, —O-phenyl, —CF$_3$, —SR$^{13}$, —S-phenyl, —SO$_2$-phenyl, —O-alkenyl or —Si (R$^{13}$)$_3$ group.

class of the xanthenes of formula (VIII):

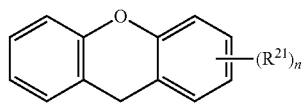

n=0 to 8, class of the xanthones of formula (IX):

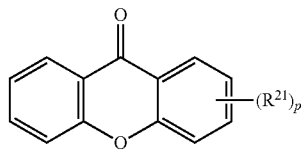

p=0 to 8 class of the naphthalene of formula (X):

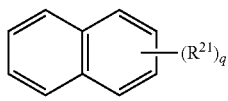

q=0 to 8 class of the anthracene of formula (XI):

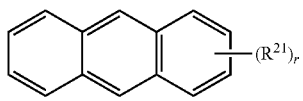

r=0 to 10 class of the phenanthrene of formula (XII):

s=0 to 10 class of the pyrene of formula (XIII):

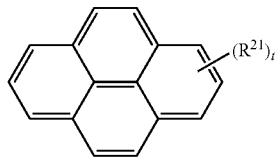

t=0 to 10 class of the fluorene of formula (XIV):

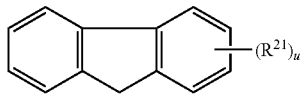

u=0 to 9 class of the fluoranthene of formula (XV):

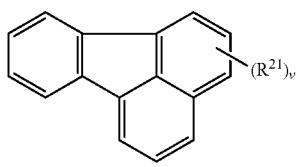

v=0 to 10 class of the chrysene of formula (XVI):

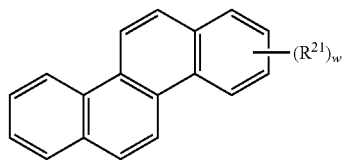

w=0 to 12 class of the fluorene of formula (XVII):

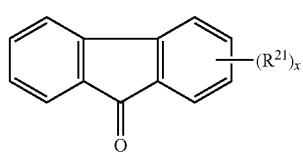

with x=0 to 8, for example 2,7-dinitro-9-fluorenone, class of the chromone of formula (XVIII):

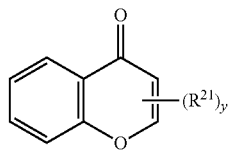

with y=0 to 6 class of the eosine of formula (XIX):

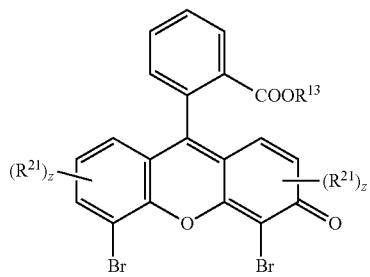

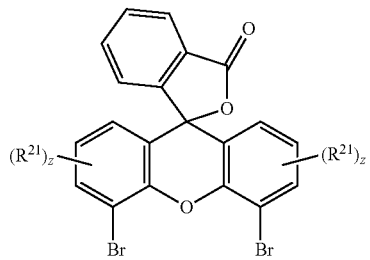

with z=0 to 5 with z=0 to 6 class of the erythrosine of formula (XX):

with z=0 to 2 or 0 to 3 class of the erythrosine of formula (XXI):

with z=0 to 3 class of the biscoumarins of formula (XXII):

with x=0 to 8 class of the thioxanthones of formula (XXIII):

with y=0 to 6 class of the thioxanthones of formula (XXIV):

with y=0 to 6

For the formulae (VIII) to (XXIII), the group $R^{21}$ has the same definition as for the molecule (VII).

Other sensitizers can be used. In particular it is possible to use the photosensitizers described in documents U.S. Pat. No. 4,939,069; U.S. Pat. No. 4,278,751; U.S. Pat. No. 4,147,552, and also the group composed of the compounds from the class of the coumarins, conjugated diketones, fluorones, amino ketones, para-aminostyryl ketones, and mixtures thereof.

According to one preferred embodiment the photosensitizer (E) is selected from the group consisting of the compounds from the class of the anthracenes, thioxanthones, camphorquinones, and phenanthrenequinone, and also mixtures thereof.

According to another preferred embodiment the dental composition comprises as photosensitizer (E) a salt of a thioxanthone substituted by at least one group containing an ammonium function. An advantage of using this type of photosensitizer is that of preventing interfering stains when the dental composition is crosslinked to produce a dental prosthesis.

According to one version of the invention, the associated anion of the salt of the thioxanthone substituted by at least one group containing an ammonium function is selected from the following anions:

a halide, $BF_4^-$, $PF_6^-$; $SbF_6^-$; the anion (III) of formula $[BX_aR_b]^-$ as defined above, $R_fSO_3^-$; $(R_fSO_2)_3C^-$ or $(R_fSO_2)_2N^-$, with $R_f$ being a linear or branched alkyl radical, substituted by at least one halogen atom, preferably a fluorine atom.

According to another version of the invention the photosensitizer (E), optionally in combination with at least one camphorquinone, a phenanthrenequinone and/or a substituted anthracene, has the following formula:

(XXV)

in which formula:
$R^{22}$ and $R^{23}$ are identical or different and represent a hydrogen or an optionally substituted C1-C10 alkyl radical, preferably R22=R23=methyl,
($X^-$) being an anionic entity, preferably a halide; $BF_4^-$; $PF_6^-$; $SbF_6^-$; the anion (III) of formula $[BX_aR_b]^-$ as defined above, R$_f$SO$_3^-$; (R$_f$SO$_2$)$_3$C$^-$ or (R$_f$SO$_2$)$_2$N$^-$, with R$_f$ being a linear or branched alkyl radical, substituted by at least one halogen atom, preferably a fluorine atom, and more preferably still (X$^-$) is selected from the borates of the following formulae: [B(C$_6$H$_3$(CF$_3$)$_2$)$_4$]$^-$ and [B(C$_6$F$_5$)$_4$]$^-$.

According to one preferred embodiment the photosensitizer (E), optionally in combination with at least one camphorquinone, a phenanthrenequinone and/or a substituted anthracene, has the following formula:

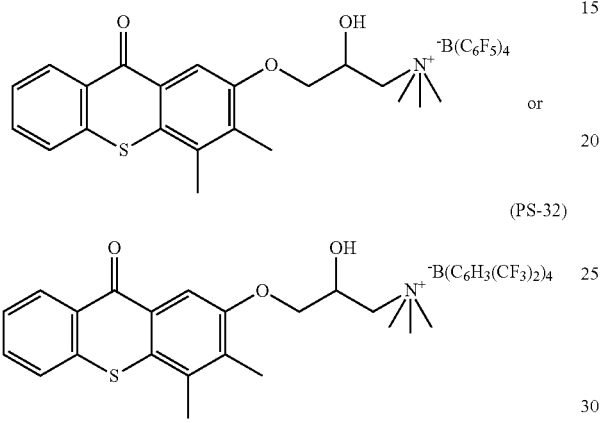

In the context of the present invention, the photosensitizers have a residual absorption for UV light of between 200 and 500 nm, preferably 400 to 500 nm, for the dental prosthesis preparations. For dental restoration, preference will be given to a photosensitizer having a residual absorption of UV light above 400 nm.

According to one preferred version, the photosensitizers will be selected from those of classes (VII), (X), (XI), (XIII), (XXIII), (XXIV) and (XXV). According to another embodiment, the photosensitizer is selected from the group consisting of the following compounds:

(PS-30): 3-(3,4-dimethyl-9-oxo-9-thioxanthenen-2-yloxy)-2-hydroxypropyl)trimethylammonium chloride;
(PS-31): 3-(3,4-dimethyl-9-oxo-9-thioxanthenen-2-yloxy)-2-hydroxypropyl)trimethylammonium tetrakis (pentafluorophenyl)borate;
(PS-32): 3-(3,4-dimethyl-9-oxo-9-thioxanthenen-2-yloxy)-2-hydroxypropyl)trimethylammonium tetrakis (bis(trifluoromethyl)phenyl)borate;
(PS-33): phenanthrenequinone;
(PS-34): camphorquinone;
(PS-35): acenaphthenequinone;
(PS-36): dibenzoyl peroxide;
(PS-37): 2-ethyl-9,10-dimethoxyanthracene;
(PS-38): 9,10-diethoxyanthracene;
(PS-39): 9,10-dibutoxyanthracene;
(PS-40): 9-hydroxymethylanthracene;
(PS-41): 2-dimethylaminothioxanthone;
(PS-42): 3-ethylcarboxyl-7-methoxythioxanthone;
(PS-43): 1-phenylthio-4-propoxythioxanthone;
(PS-44): 2-methoxythioxanthone;
(PS-45): 2-(N,N-diethylaminopropoxy)thioxanthone;
(PS-46): 2-isopropylthioxanthone;
(PS-47): 1-chloro-4-propoxythioxanthone;
(PS-48): 4-isopropylthioxanthone;

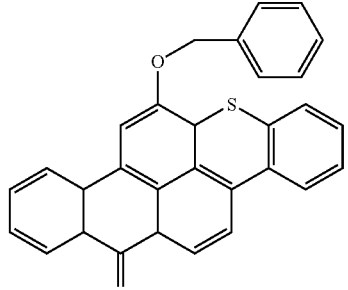

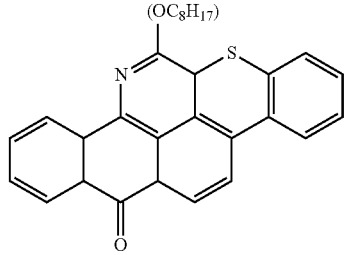

and mixtures thereof.

In the context of the invention, the material obtained after crosslinking exhibits a significantly improved storage stability. When the thioxanthones of the class described by the formula (XXV) are employed, an additional advantage is noted in using the thioxanthones (PS-31) or (PS-32), optionally in combination with at least one camphorquinone, a phenanthrenequinone and/or a substituted anthracene, which is the absence of residual coloration.

Besides the reinforcing fillers, pigments may be used to color the dental composition in accordance with the intended use and ethnic groups.

For example, red pigments are used in the presence of microfibers for the dental compositions used for preparing dental prostheses, in order to simulate blood vessels.

Use is also made of pigments based on metal oxides (iron oxides and/or titanium oxide and/or aluminum oxide and/or zirconium oxide, etc.) for the dental compositions used for preparing restoration material, so as to give an ivory-colored crosslinked material.

Other additives may be incorporated into dental compositions according to the invention. Examples include biocides, stabilizers, flavors, plasticizers, and adhesion promoters. Among the additives that may be considered, use will be made advantageously of organic coreactants which are crosslinkable and/or polymerizable. These coreactants are liquid at ambient temperature or thermofusible at a temperature lower than 100° C., and each coreactant comprises at least two reactive functions such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyl, dioxolane-dioxolane-alcohol, etc. Examples include the resins R70 and R71.

The dental compositions according to the invention may be used for numerous dental applications, and especially in the field of dental prostheses, in the field of dental restoration, and in the field of temporary teeth.

The dental composition according to the invention is preferably in the form of a single product comprising the various components ("monocomponent"), thereby facilitating its employment, particularly in the field of dental prostheses. If appropriate the stability of this product may be ensured by means of amine-functional organic derivatives in accordance with the teaching of document WO 98/07798.

In the field of dental prostheses, the product in the "monocomponent" form may be deposited with the aid of a syringe directly on the plaster model or in a core. It is then polymerized (polymerization by possible successive layers) with the aid of a UV lamp (visible light spectrum 400-500 nm).

In general it is possible to produce an esthetic and durable dental prosthesis in 10 to 15 minutes.

It should be noted that the products obtained from the dental composition according to the invention are nonporous. Hence, after optional polishing with the aid of a felt brush, for example, the surface of the dental prostheses obtained is smooth and shiny and therefore does not require the use of varnish.

The applications in the field of dental prostheses are essentially those of the attached prosthesis, and can be divided into two types:
  total prosthesis in the case of a patient with no teeth at all;
  partial prosthesis owing to the absence of several teeth, resulting either in a temporary prosthesis or in a skeleton brace.

In the field of dental restoration, the dental composition according to the invention may be used as material for filling the anterior and posterior teeth in different colors (for example, "VITA" colors), and is rapid and easy to use.

Since the dental composition is nontoxic and can be polymerized in thick layers, it is not essential to polymerize the material in successive layers. In general a single injection of the dental composition is sufficient.

The preparations for dental prostheses and for restoration materials are carried out according to the usual techniques of the art.

In the case of application of the dental composition to a tooth, either the tooth may be pretreated with a mordant and then with a bonding primer, which may itself be photo-crosslinkable, or else the dental composition may be prepared as a mixture with a bonding primer prior to its use.

The invention also relates to a process (I) for treating a dental filler (B) comprising the following steps:
  a) in a solvent medium the dental filler (B) and at least one organosilicon coupling agent (F) as defined in claim 1 are mixed,
  b) the solvent is removed by filtration to give an intermediate dental filler (B-1),
  c) the intermediate dental filler (B-1) undergoes a heat treatment to terminate the coupling reaction between the intermediate dental filler (B-1) and the coupling agent (F) and so to obtain an intermediate dental filler (B-2),
  d) the intermediate dental filler (B-2) is then mixed in a solvent medium with at least one compound (G) as defined in claim 1 and in the presence of at least one dispersant (H) as defined in claim 1, 2 or 3,
  e) the solvent is removed by filtration to give an intermediate dental filler (B-3), and
  f) the intermediate dental filler (B-3) undergoes a heat treatment to terminate the reaction between the intermediate dental filler (B-3) and the compound (G) and so to obtain a treated dental filler (B).

According to another embodiment, the invention provides a process (II) for treating a dental filler (B), comprising the following steps:

a) in a solvent medium the dental filler (B) and at least one organosilicon coupling agent (F) as defined in claim 1 are mixed,
  b) the solvent is removed by filtration to give an intermediate dental filler (B-1),
  c) the intermediate dental filler (B-1) undergoes a heat treatment to terminate the coupling reaction between the intermediate dental filler (B-1) and the coupling agent (F) and so to obtain an intermediate dental filler (B-2),
  d) the intermediate dental filler (B-2) is then mixed in a solvent medium with at least one compound (G) as defined in claim 1,
  e) the solvent is removed by filtration to give an intermediate dental filler (B-3),
  f) the intermediate dental filler (B-3) undergoes a heat treatment to terminate the reaction between the intermediate dental filler (B-3) and the compound (G) and so to obtain an intermediate filler (B-5),
  g) the intermediate dental filler (B-5) is then mixed in a solvent medium with at least one compound (G) as defined in claim 1 and in the presence of at least one dispersant (H) as defined in claim 1, 2 or 3,
  h) the solvent is removed by filtration to give an intermediate dental filler (B-6), and
  i) the intermediate dental filler (B-6) undergoes a heat treatment to terminate the reaction between the intermediate dental filler (B-6) and the compound (G) and so to obtain a treated dental filler (B).

According to one preferred embodiment the heat treatment of steps c) and f) of the processes (I) and (II) take place by heating to a temperature less than or equal to 200° C., preferably less than or equal to 160° C. and more preferably between 100 and 165° C.

The organosilicon coupling agent (F), the compound (G), the dispersant (H), and the dental reinforcing filler (B) are as defined in the dental composition according to the invention.

The invention likewise provides a reinforcing filler obtainable by the process according to the invention, and its use in dental compositions.

A further subject of the invention relates to the use of a dental composition according to the invention for producing dental prostheses or for dental restoration.

Another subject of the invention relates to a dental prosthesis obtainable by crosslinking a composition according to the invention.

A final object of the invention relates to a dental restoration material obtainable by crosslinking a composition according to the invention.

The examples below are given by way of illustration. They make it possible in particular to understand the invention more clearly and to highlight some of its advantages and to illustrate a number of its embodiment versions.

EXAMPLES

Structures

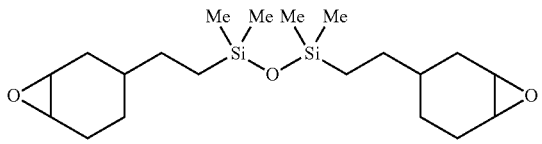

(S-1)

-continued

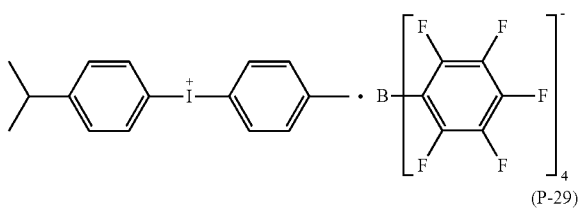

(P-22)

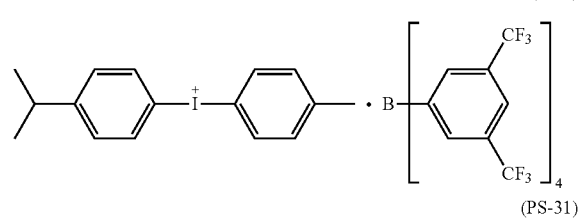

(P-29)

(PS-31)

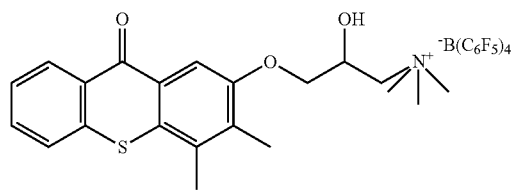

Compound (S-96) sold by the company Dow Chemical under the name UVR-6105

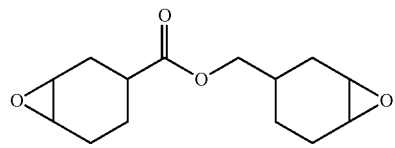

(S-96)

Filler (B-i): quartz glass (particle size=1.5 µm, SiO$_2$ 56%; SrO 14%; B$_2$O$_3$ 14%; Al$_2$O$_3$ 14%; F 2%), sold by the company Schott under the name G018-163 Filler (B-ii): quartz glass (particle size=1.5 µm, SiO$_2$ 55%; BaO 25%; B$_2$O$_3$ 10%; Al$_2$O$_3$ 10%), sold by the company Schott under the name GM27-884.

Dispersant (H): Disperbyk-164° (sold by the company Byk).

Dispersant (C): Disperbyk-164° (sold by the company Byk).

Example 1-1 and 1-2

Treatment of a Dental Filler According to the Invention

Example 1-1 a) A flask is charged with 200 g of filler (B-i), to which are added 200 g of acetone and then 7.3 g of silane glycidyloxypropyltrimethoxysilane or GLYMO. The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives an intermediate filler (B-2).

b) A flask is charged with 180 g of filler (B-2), to which are added 180 g of acetone and then 31.5 g of the oxirane-functional compound (S-1) (for example 1-2, only 15.8 g of the oxirane-functional compound (S-1) and also 15.8 g of compound (S-96) are added) and 0.85 g of a 60% solution of dispersant (H) in a solvent. The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives a dental filler (B-i) treated according to the invention.

Example 2

Treatment of a Dental Filler According to the Invention a) A flask is charged with 200 g of filler (B-i), to which are added 200 g of acetone and then 7.3 g of silane glycidyloxypropyltrimethoxysilane or GLYMO. The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives an intermediate filler (B-2).

b) A flask is charged with 180 g of filler (B-2), to which are added 180 g of acetone and then 15.8 g of the oxirane-functional compound (S-1) and 15.8 g of compound (S-96). The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives an intermediate dental filler (B-5).

c) A flask is charged with 180 g of filler (B-5), to which are added 160 g of acetone and then 28.1 g of the oxirane-functional compound (S-1) and 0.75 g of a 60% solution of dispersant (H) in a solvent. The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives a dental filler (B-i) treated according to the invention.

Example 3 (Comparative)

Treatment of a Filler According to International Application WO-A-2005121200 a) A flask is charged with 200 g of filler (B-i), to which are added 200 g of acetone and then 7.3 g of silane glycidyloxypropyltrimethoxysilane or GLYMO. The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives an intermediate filler (B-2).

b) A flask is charged with 180 g of filler (B-2), to which are added 180 g of acetone and then 15.8 g of the oxirane-functional compound (S-1) and 15.8 g of compound (S-96). The constituents are mixed for two hours with propeller stirring at ambient temperature under nitrogen. The mixture is poured into a Buchner funnel equipped with a filter (0.22 micron). The dental filler is recovered, and is then ground using a mortar and pestle and subsequently screened on a 200 micron cloth. The dental filler is then dried in an oven at 110° C. for 16 h. On exit from the oven, the filler is cooled to ambient temperature for 30 minutes. This gives a dental filler treated according to International application WO-A-2005121200.

Example 4

Formulations of Dental Compositions

A flask is charged with 0.09 g of the photosensitizer of formula (PS-31), to which are added 0.13 g of the photosensitizer 9,10-dibutoxyanthracene (PS-39), 0.13 g of the photosensitizer camphorquinone (PS-34), 3.87 g of photoinitiator (P-22), 195.1 g of oxirane-functional siloxane resin (S-1); finally, 0.58 g of a 60% solution of dispersant (C) in a solvent is added. This formulation is stirred using a magnetic bar for approximately 24 hours.

7.75 g of the formulation prepared above are charged to a mortar, and 17.25 g of a dental filler are added:
- for formulation 1 (comparative): filler=filler (B-i) untreated;
- for formulation 2 (inventive): filler=filler (B-i) treated according to example 1-1;
- for formulation 3 (inventive): filler=filler (B-i) treated according to example 1-2;
- for formulation 4 (inventive): filler=filler (B-i) treated according to example 2;
- for formulation 5 (comparative): filler=filler (B-ii) treated according to example 3; and the mixture is kneaded using a mortar and a pestle.

Subsequently the change in the epoxy content over time is monitored in the formulations prior to crosslinking, the formulations being placed in an oven at 40° C. (accelerated aging and simulation of prolonged storage). The results are set out in table I below:

TABLE I

Epoxy content (mEE = milliequivalents of epoxy) after aging for x days at 40° C.

| Number of days (x) at 40° C. | Formulation 1 Comparative | Formulation 5 Comparative | Formulation 4 Inventive | Formulation 3 Inventive | Formulation 2 Inventive |
|---|---|---|---|---|---|
| 0 | 138 | 130 | 143 | 171 | 154 |
| 1 | 69 | 126 | 142 | 170 | 153 |
| 4 |  | 111 | 138 | 168 | 150 |
| 6 |  | 102 | 136 | 167 | 148 |
| 12 |  |  | 129 | 162 | 143 |
| 20 |  |  | 121 | 157 | 136 |
| 30 |  |  | 110 | 150 | 128 |
| 35 |  |  | 104 | 146 | 123 |
| 40 |  |  | 99 | 142 | 119 |
| 50 |  |  |  | 135 |  |

The following is noted:
- the acceptable limit for use is approximately 100 mEE; below this threshold, the formulation is in a hardened form and can no longer be used in that state;
- for a formulation based on an untreated filler (formulation 1), the epoxy content measured falls by nearly 50% after 24 h of accelerated aging at 40° C. This indicates that the formulation is not stable, since the epoxy functions have reacted (harmful hardening of the formulation);
- for a formulation based on a filler treated in accordance with International application WO-A-2005121200 (formulation 5), the epoxy content measured falls by nearly 30% after 6 days of accelerated aging at 40° C.; and
- for the formulations according to the invention (formulations 2, 3 and 4), the epoxy contents are more stable, preventing premature hardening of the formulations in the course of a prolonged storage.

The invention claimed is:
1. A dental composition comprising:
(1) at least one cationically reactive compound (A),
(2) at least one pretreated dental filler comprising a dental filler (B) pretreated with ingredients (a), (b), and (c) in a solvent medium:
 (a) at least one compound (G) which is:
  an organic monomer, oligomer or polymer, or
  an organosiloxane monomer, oligomer or polymer,
  said compound (G) comprising at least one reactive oxirane, oxetane, alkenyl ether and/or carbonate function (frC),
 (b) at least one organosilicon coupling agent (F) comprising at least one reactive function (frA) bonded directly to a silicon atom capable of reacting with the dental filler (B), and at least one reactive function (frB) not directly bonded to a silicon atom capable of reacting with a reactive function (frC) of the compound (G), and
 (c) at least one dispersant (H) which maintains the dental filler (B) in a nonagglomerated form during and/or after the treatment in a solvent medium,
(3) optionally at least one dental filler (B'),
(4) optionally at least one dispersant (C), comprising at least one organic polymer or copolymer;
(5) at least one cationic photoinitiator (D); and
(6) optionally at least one photosensitizer (E),
wherein said composition has increased stability during aging as indicated by having an epoxy content, expressed as milliequivalents (mEE) of epoxy, of 100 or greater, after aging for 30 days at 40° C.
2. The dental composition of claim 1, wherein the dispersant (H) is an organic polymer or copolymer or a carboxylic acid monodiester.

3. The dental composition of claim 1, wherein the dispersant (H) is selected from the group consisting of:
acrylic polymers, optionally in the form of a salt with an alkylammonium, polyesters, polyethers, polyurethanes, modified polyurethanes, and polyacrylate polyols, copolymers thereof,
carboxylic acid monoesters,
polyurethane/acrylate copolymers, optionally in the form of a salt with an alkylammonium, and
mixtures thereof.

4. The dental composition of claim 1, wherein said at least one dental filler (B) having been treated by a process (I) comprising:
a) mixing in a solvent medium the at least one dental filler (B) and at least one organosilicon coupling agent (F),
b) forming an intermediate dental filler (B-1) by removing the solvent by filtration,
c) obtaining an intermediate dental filler (B-2) by heat treating the intermediate dental filler (B-1) to terminate the coupling reaction between the intermediate dental filler (B-1) and the coupling agent (F),
d) mixing the intermediate dental filler (B-2) in a solvent medium with at least one compound (G) and in the presence of at least one dispersant (H),
e) forming an intermediate dental filler (B-3) by removing the solvent by filtration, and
f) forming the pretreated dental filler by heat treating the intermediate dental filler (B-3) to terminate the reaction between the intermediate dental filler (B-3) and the compound (G).

5. The dental composition of claim 1, wherein at least one dental filler (B) is treated by a process (II) comprising:
a) mixing in a solvent medium the dental filler (B) and at least one organosilicon coupling agent (F),
b) forming an intermediate dental filler (B-1) by removing the solvent by filtration,
c) obtaining an intermediate dental filler (B-2) by heat treating the intermediate dental filler (B-1) to terminate the coupling reaction between the intermediate dental filler (B-1) and the coupling agent (F),
d) mixing the intermediate dental filler (B-2) in a solvent medium with at least one compound (G),
e) forming an intermediate dental filler (B-3) by removing the solvent by filtration,
f) forming an intermediate dental filler (B-5) by heat treating the intermediate dental filler (B-3) to terminate the reaction between the intermediate dental filler (B-3) and the compound (G),
g) mixing the intermediate dental filler (B-5) in a solvent medium with at least one compound (G) in the presence of at least one dispersant (H),
h) forming an intermediate dental filler (B-6) by removing the solvent by filtration, and
i) obtaining a pretreated dental filler by heat treating the intermediate dental filler (B-6) to terminate the reaction between the intermediate dental filler (B-6) and the compound (G).

6. The dental composition of claim 4, wherein the heat treatments of steps c), f) and i) of processes (I) and (II) take place by heating to a temperature less than or equal to 200° C.

7. The dental composition of claim 1, wherein:
the reactive function (frA) bonded directly to a silicon atom of the organisilicon coupling agent (F) is an alkoxy, epoxy or hydroxyl function;
the reactive function (frB) not bonded directly to a silicon atom of the organosilicon coupling agent (F) is an oxirane, oxetane, hydroxyl, acid, carboxylic acid anhydride or diol function; and
the reactive function (frC) of the compound (G) is an oxirane, oxetane, alkenyl ether or carbonate function.

8. The dental composition of claim 1, wherein the organosilicon coupling agent (F) is selected from the group consisting of glycidyloxypropyltrimethoxysilane, the product of hydrolysis of glycidyloxypropyltrimethoxysilane; glycidyloxypropyltriethoxysilane, the product of hydrolysis in acidic medium of glycidyloxypropyltriethoxysilane; glycidyloxypropyldimethoxymethylsilane or the product of hydrolysis, beta-(3,4-epoxycyclohexyl)ethyltriethoxysilane or the product of hydrolysis, and beta-(3,4-epoxycyclohexyl)ethyltrimethoxysilane or the product of hydrolysis.

9. The dental composition of claim 1, wherein the compound (G) is a silicone oligomer (G-1) or a silicone polymer (G-2) comprising at least one reactive oxirane, oxetane, alkenyl ether and/or carbonate function (frC).

10. The dental composition of claim 9, wherein the silicone oligomer (G-1) or the silicone polymer (G-2) comprise:
a) at least one unit of formula:

(M-13)

in which formula:
a=0, 1 or 2,
the radicals $R^0$, which may be identical or different are each an alkyl, cycloalkyl, aryl, vinyl, hydrogeno or alkoxy radical,
the radicals Z, which may be identical or different, are each an organic substituent containing at least one oxirane, alkenyl ether, oxetane and/or carbonate function, and
b) at least two silicon atoms.

11. The dental composition of claim 10, wherein the silicone oligomer (G-1) or the silicone polymer (G-2) are selected from the group consisting of the compounds of formulae (S-1) to (S-15) below:

a)

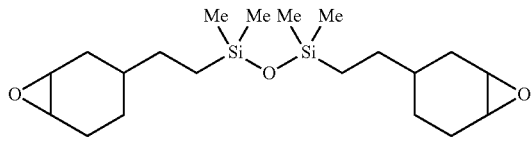

(S-1)

b)

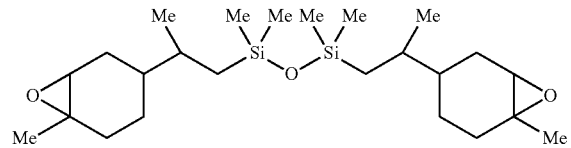

(S-2)

-continued
c)
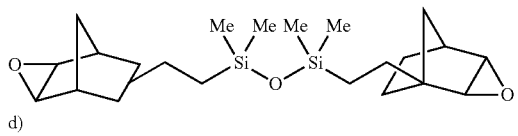
(S-3)
d)
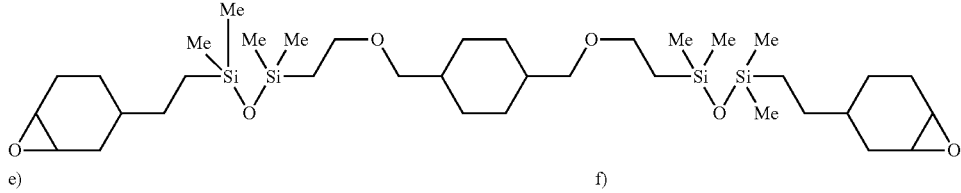
(S-4)
e)
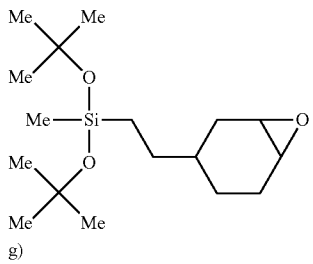
(S-5)
f)
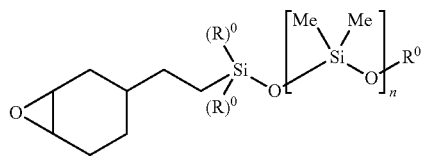
(S-6)
(n < 1000)
g)
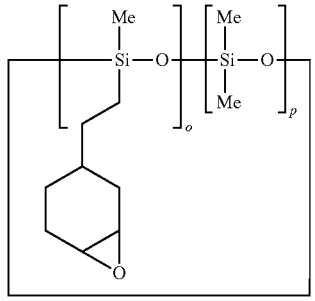
(S-7)
(o + p) < 10
o > 1
h)
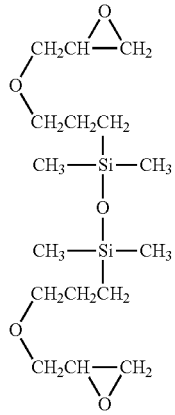
(S-8)
i)
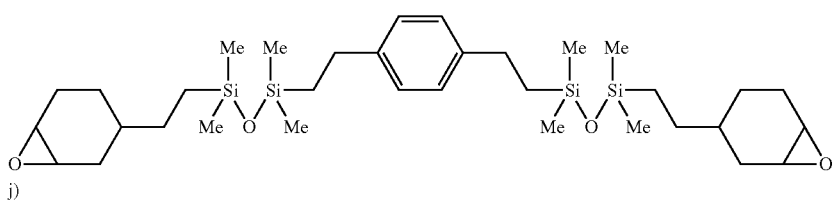
(S-9)
j)
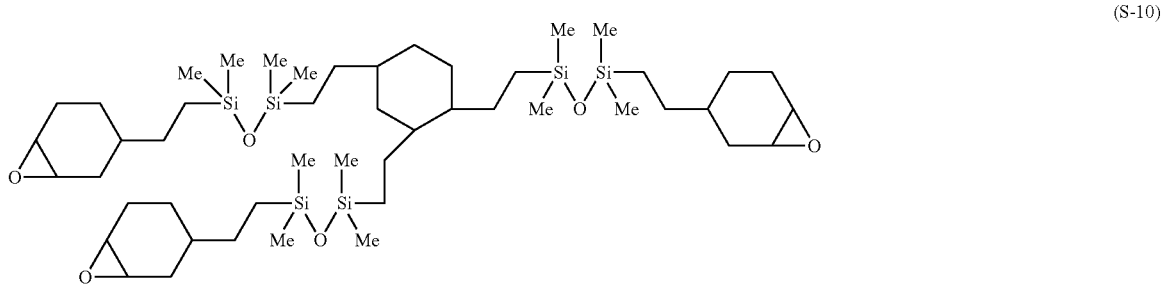
(S-10)

k)
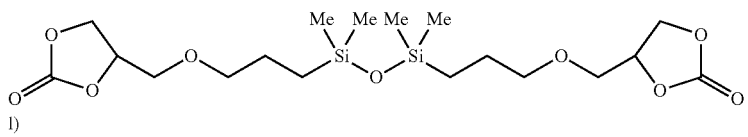
(S-11)
l)
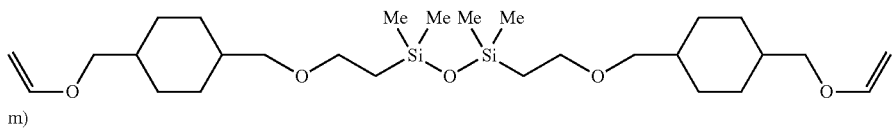
(S-12)
m)
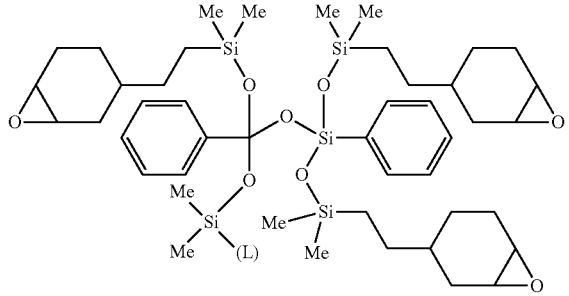
(S-13)
L=H: OH: Me; phenyl; $C_1$-$C_{12}$ alkyl; $C_1$-$C_6$ cycloalkyl;
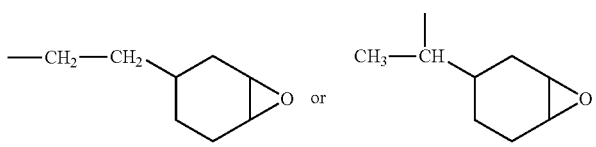
n)
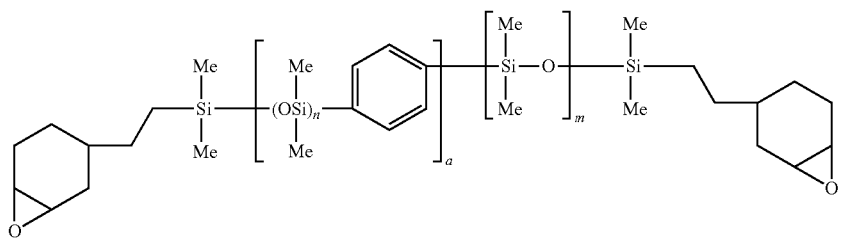
(S-14)
with n<100; a<100 and m<100
o)
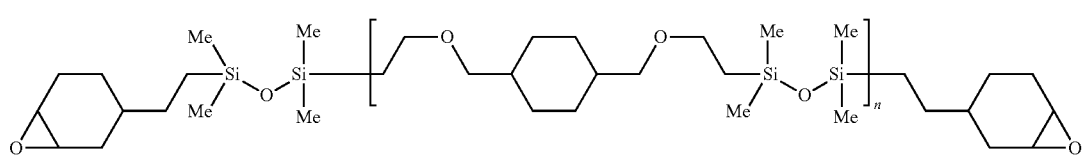
(S-15)
with n < 100 in which formulae R° or R⁰, which are identical or different, represent an alkyl, cycloalkyl or aryl radical.

12. The composition of claim 1, wherein the cationic photoinitiator (D) is selected from the group consisting of:
(P-16): $[(C_8H_{17})-O-C_6H_4-I-C_6H_5)]^+$, $[B(C_6F_5)_4]^-$;
(P-17): $[C_{12}H_{25}-C_6H_4-I-C_6H_5]^+$, $[B(C_6F_5)_4]^-$;
(P-18): $[(C_8H_{17}-O-C_6H_4)_2I]^+$, $[B(C_6F_5)_4]^-$;
(P-19): $[(C_8H_{17}-O-C_6H_4-I-C_6H_5)]^+$, $[B(C_6F_5)_4]^-$;
(P-20): $[(C_6H_5)_2S-C_6H_4-O-C_8H_{17}]^+$, $[B(C_6H_4CF_3)_4]^-$;
(P-21): $[(C_{12}H_{25}-C_6H_4)_2I]^+$, $[B(C_6F_5)_4]^-$;
(P-22): $[(CH_3-C_6H_4-I-C_6H_4-CH(CH_3)_2]^+$, $[B(C_6F_5)_4]^-$;
(P-23): $(\eta 5\text{-cyclopentadienyl})(\eta 6\text{-toluene})Fe^+$, $[B(C_6F_5)_4]^-$;
(P-24): $(\eta 5\text{-cyclopentadienyl})(\eta 6\text{-1-methylnaphthalene})Fe^+$, $[B(C_6F_5)_4]^-$;
(P-25): $(\eta 5\text{-cyclopentadienyl})(\eta 6\text{-cumene})Fe^+$, $[B(C_6F_5)_4]^-$;
(P-26): $[(C_{12}H_{25}-C_6H_4)_2I]^+$, $[B(C_6H_3(CF_3)_2]^-$;
(P-27): $[CH_3-C_6H_4-I-C_6H_4-CH_2CH(CH_3)_2]^+$, $[B(C_6F_5)_4]^-$;
(P-28): $[CH_3-C_6H_4-I-C_6H_4-CH_2CH(CH_3)_2]^+$, $[B(C_6H_3(CF_3)_2)_4]^-$; and
(P-29): $[CH_3-C_6H_4-I-C_6H_4-CH(CH_3)_2]^+$, $[B(C_6H_3(CH_3)_2)_4]^-$.

13. The dental composition of claim 1, wherein the cationic photoinitiator (D) is an iodonium salt.

14. The dental composition of claim 1, wherein the photosensitizer (E) comprises in its structure one or more substituted or unsubstituted aromatic nuclei, having a residual absorption for light of between 200 and 500 nm.

15. The dental composition of claim 1, wherein the photosensitizer (E) is selected from the group consisting of the anthracenes, thioxanthones, camphorquinones and phenanthrenequinone and mixtures thereof.

16. The dental composition of claim 1, wherein the dental filler (B) is an inorganic glass or a fumed silica.

17. A process for producing a pretreated dental filler pretreated with ingredients (a), (b), and (c):
(a) at least one compound (G) which is:
an organic monomer, oligomer or polymer, or
an organosiloxane monomer, oligomer or polymer, said compound (G) comprising at least one reactive oxirane, oxetane, alkenyl ether and/or carbonate function (frC),
(b) at least one organosilicon coupling agent (F) comprising at least one reactive function (frA) bonded directly to a silicon atom capable of reacting with the dental filler (B), and at least one reactive function (frB) not directly bonded to a silicon atom capable of reacting with a reactive function (frC) of the compound (G), and
(c) at least one dispersant (H) which maintains the dental filler (B) in a nonagglomerated form during and/or after the treatment in a solvent medium,
said process comprising:
a) mixing in a solvent medium a dental filler and at least one organosilicon coupling agent (F),
b) forming an intermediate dental filler (B-1) by removing the solvent by filtration,
c) forming an intermediate dental filler (B-2) by heat treating the intermediate dental filler (B-1) to terminate the coupling reaction between the intermediate dental filler (B-I) and the coupling agent (F),
d) mixing the intermediate dental filler (B-2) in a solvent medium with at least one compound (G) and in the presence of at least one dispersant (H),
e) forming an intermediate dental filler (B-3) by removing the solvent by filtration, and
f) obtaining a pretreated dental filler by heat treating the intermediate dental filler (B-3) to terminate the reaction between the intermediate dental filler (B-3) and the compound (G),
wherein said pretreated dental filler has increased stability during aging as indicated by having an epoxy content, expressed as milliequivalents (mEE) of epoxy, of 100 or greater, after aging for 30 days at 40° C.

18. A process for producing a dental filler pretreated with ingredients (a), (b), and (c):
(a) at least one compound (G) which is:
an organic monomer, oligomer or polymer, or
an organosiloxane monomer, oligomer or polymer,
said compound (G) comprising at least one reactive oxirane, oxetane, alkenyl ether and/or carbonate function (frC),
(b) at least one organosilicon coupling agent (F) comprising at least one reactive function (frA) bonded directly to a silicon atom capable of reacting with the dental filler (B), and at least one reactive function (frB) not directly bonded to a silicon atom capable of reacting with a reactive function (frC) of the compound (G), and
(c) at least one dispersant (H) which maintains the dental filler (B) in a nonagglomerated form during and/or after the treatment in a solvent medium,
said process comprising:
a) mixing in a solvent medium a dental filler and at least one organosilicon coupling agent (F),
b) forming an intermediate dental filler (B-1) by removing the solvent by filtration,
c) forming an intermediate dental filler (B-2) by heat treating the intermediate dental filler (B-1) to terminate the coupling reaction between the intermediate dental filler (B-1) and the coupling agent (F),
d) mixing the intermediate dental filler (B-2) in a solvent medium with at least one compound (G) as defined in claim 1,
e) forming an intermediate dental filler (B-3) by removing the solvent by filtration,
f) forming an intermediate dental filler (B-5) by heat treating the intermediate dental filler (B-3) to terminate the reaction between the intermediate dental filler (B-3) and the compound (G),
g) mixing the intermediate dental filler (B-5) in a solvent medium with at least one compound (G) and in the presence of at least one dispersant (H),
h) forming an intermediate dental filler (B-6) by removing the solvent is by filtration, and
i) obtaining a pretreated dental filler by heat treating the intermediate dental filler (B-6) to terminate the reaction between the intermediate dental filler (B-6) and the compound (G),
wherein said pretreated dental filler has increased stability during aging as indicated by having an epoxy content, expressed as milliequivalents (mEE) of epoxy, of 100 or greater, after aging for 30 days at 40° C.

19. A dental filler prepared by the process of claim 17.

20. A dental composition comprising the dental filler of claim 19.

21. A method for producing a dental prostheses or a dental restoration material comprising shaping the composition of claim 1 into the structure of a tooth.

22. A dental prosthesis comprising a cross-linked composition of claim 1.

23. A dental restoration material comprising a cross-linked composition of claim 1.

24. A dental filler prepared by the process of claim 18.

25. A dental composition comprising:

(1) at least one cationically reactive compound (A)

(2) at least one pretreated dental filler comprising a dental filler (B) linked to at least one organosilicon coupling agent (F), wherein the at least one organosilicon coupling agent (F) is coupled to at least one compound (G) in the presence of at least one dispersant (H), which maintains the dental filler (B) in a nonagglomerated form during and/or after the treatment in a solvent medium, (3) optionally at least one dental filler (B'), (4) optionally at least one dispersant (C), comprising at least one organic polymer or copolymer;

(5) at least one cationic photoinitiator (D); and (6) optionally at least one photosensitizer (E), wherein said at least one organosilicon coupling agent (F) comprising at least one reactive function (frA) bonded directly to a silicon atom capable of reacting with the dental filler (B), and at least one reactive function (frB) not directly bonded to a silicon atom capable of reacting with a reactive function (frC) of the compound (G), and said at least one compound (G) is an organic monomer, oligomer or polymer, or an organosiloxane monomer, oligomer or polymer, and said compound (G) comprises at least one reactive oxirane, oxetane, alkenyl ether and/or carbonate function (frC), wherein said composition has increased stability during aging as indicated by having an epoxy content, expressed as milliequivalents (mEE) of epoxy, of 100 or greater, after aging for 30 days at 40°.

26. A dental composition comprising the dental filler as defined by claim 25.

* * * * *